(12) United States Patent
Zoller et al.

(10) Patent No.: US 8,357,499 B2
(45) Date of Patent: Jan. 22, 2013

(54) EXPRESSION OF FUNCTIONAL HUMAN OLFACTORY CYCLIC NUCLEOTIDE GATED (CNG) CHANNEL IN RECOMBINANT HOST CELLS AND USE THEREOF IN CELL BASED ASSAYS TO IDENTIFY SMELL MODULATORS

(75) Inventors: Mark Zoller, La Jolla, CA (US); Hong Xu, San Diego, CA (US); Lena Staszewski, San Diego, CA (US); Bryan Moyer, Thousand Oaks, CA (US); Alexey Pronin, San Diego, CA (US); Jon Elliot Adler, Sherwood, OR (US); Guy Servant, San Diego, CA (US); Nicholas Callamaras, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 1553 days.

(21) Appl. No.: 11/326,441

(22) Filed: Jan. 6, 2006

(65) Prior Publication Data

US 2011/0224095 A1    Sep. 15, 2011

Related U.S. Application Data

(62) Division of application No. 10/189,507, filed on Jul. 8, 2002, now Pat. No. 7,052,857.

(60) Provisional application No. 60/303,140, filed on Jul. 6, 2001, provisional application No. 60/337,154, filed on Dec. 10, 2001.

(51) Int. Cl.
  *G01N 33/567* (2006.01)
  *C07K 14/705* (2006.01)
  *C12N 15/12* (2006.01)
(52) U.S. Cl. .......... 435/7.21; 435/7.1; 435/7.2; 436/501
(58) Field of Classification Search .................. None
  See application file for complete search history.

(56) References Cited

U.S. PATENT DOCUMENTS 5,993,778 A    11/1999    Firestein et al.

FOREIGN PATENT DOCUMENTS

WO    00/06593    2/2000
WO    02/064631 A2    8/2002

OTHER PUBLICATIONS

Wolfgang Bönigk, et al., "The Native Rat Olfactory Cyclic Nucleotide-Gated Channel is Composed of Three Distinct Subunits", The Journal of Neuroscience, vol. 19, No. 136, p. 5332-5347, Jul. 1, 1999.
Jean-Pierre Montmayeur, et al., "A Candidate Taste Receptor Gene Near a Sweet Taste Locus", Nature Neuroscience, vol. 4, No. 5, May 2001.
Michinori Kitagawa, et al., "Molecular Genetic Identification of a Candidate Receptor Gene for Sweet Taste", Biochemical and Biophysical Research Communications, vol. 283, p. 236-242, 2001.
Marianna Max, et al., "Tas1r3, encoding a new candidate taste receptor, is allelic to the sweet responsiveness locus Sac", Nature Genetics, vol. 28, p. 58-63, May 2001.
Eduardo Sainz, et al., "Identification of a Novel Member of the T1R family of putative taste receptors", Journal of Neurochemistry, vol. 77, p. 896-903, 2001.
Claire Johnson, et al., "The Effect of the Sweetness Inhibitor 2(-4-methoxyphenoxy) propanoic acid (sodium salt) (Na-PMP) on the taste of bitter-sweet stimuli", Chemical Senses, vol. 19, No. 4, p. 349-358, 1994.
Sue C. Kinnamon and Thomas A. Cummings, "Chemosensory Transduction Mechanisms in Taste", Annu. Rev. Physoil., vol. 54, p. 715-731, 1992.

*Primary Examiner* — John Ulm
(74) *Attorney, Agent, or Firm* — Hunton & Williams LLP

(57) ABSTRACT

The present invention relates to isolated nucleic acid sequences that encode human olfactory cyclic nucleotide gated (CNG) channel subunits, and the corresponding polypeptides. The invention further relates to the use of human CNG channels to profile, screen for, and identify compounds that modulate the human olfactory CNG channel. More specifically, the invention relates to the expression of the human olfactory CNG channel in cells, preferably mammalian cells, and the use of these cells in high throughput cell-based assays to identify compounds that enhance or block human olfactory CNG function. Compounds that activate the olfactory CNG channel will enhance smell and can be used to make foods more palatable for individuals with attenuated olfactory function. Conversely, compounds that inhibit the olfactory CNG channel will inhibit smell and can be use to block malodors. Additionally, the invention relates to the use of cell-based olfactory CNG channel assays to identify modulates of G-protein coupled receptor (GPCRs) and other proteins that regulate cyclic nucleotide levels.

17 Claims, 12 Drawing Sheets

FIG. 1 hOCNC1

```
ATGACCGAAAAAACCAATGGTGTGAAGAGCTCCCCAGCCAATAATCACAACCATCA
TGCACCTCCTGCCATCAAGGCCAATGGCAAAGATGACCACAGGACAAGCAGCAGGC
CACACTCTGCAGCTGACGATGACACCTCCTCAGAACTGCAGAGGCTGGCAGACGTG
GATGCCCCACAGCAGGGAAGGAGTGGCTTCCGCAGGATAGTTCGCCTGGTGGGGAT
CATCAGAGAATGGGCCAACAAGAATTTCCGAGAGGAGGAACCTAGGCCTGACTCAT
TCCTCGAGCGTTTTCGTGGGCCTGAACTCCAGACTGTGACCACACAGGAGGGGGATG
GCAAAGGCGACAAGGATGGCGAGGACAAAGGCACCAAGAAGAAATTTGAACTATT
TGTCTTGGACCCAGCTGGGGATTGGTACTACTGCTGGCTATTTGTCATTGCCATGCCC
GTCCTTTACAACTGGTGCCTGCTGGTGGCCAGAGCCTGCTTCAGTGACCTACAGAAA
GGCTACTACCTGGTGTGGCTGGTGCTGGATTATGTCTCAGATGTGGTCTACATTGCG
GACCTCTTCATCCGATTGCGCACAGGTTTCCTGGAGCAGGGGCTGCTGGTCAAAGAT
ACCAAGAAACTGCGAGACAACTACATCCACACCCTGCAGTTCAAGCTGGATGTGGC
TTCCATCATCCCCACTGACCTGATCTATTTTGCTGTGGACATCCACAGCCCTGAGGTG
CGCTTCAACCGCCTGCTGCACTTTGCCCGCATGTTTGAGTTCTTTGACCGGACAGAG
ACACGCACCAACTACCCTAACATCTTCCGCATCAGCAACCTTGTCCTCTACATCTTG
GTCATCATCCACTGGAATGCCTGCATCTATTATGCCATCTCCAAATCCATAGGCTTTG
GGGTCGACACCTGGTTACCCAAACATCACTGACCCTGAGTATGGCTACCTGGCTA
GGGAATACATCTATTGCCTTTACTGGTCCACACTGACTCTCACTACCATTGGGGAGA
CACCACCCCCTGTAAAGGATGAGGAGTACCTATTTGTCATCTTTGACTTCCTGATTG
GCGTCCTCATCTTTGCCACCATCGTGGGAAATGTGGGCTCCATGATCTCCAACATGA
ATGCCACCCGGGCAGAGTTCCAGGCTAAGATCGATGCCGTGAAACACTACATGCAG
TTCCGAAAGGTCAGCAAGGGGATGGAAGCCAAGGTCATTAGGTGGTTTGACTACTT
GTGGACCAATAAGAAGACAGTGGATGAGCGAGAAATTCTCAAGAATCTGCCAGCCA
AGCTCAGGGCTGAGATAGCCATCAATGTCCACTTGTCCACACTCAAGAAAGTGCGC
ATCTTCCATGATTGTGAGGCTGGCCTGCTGGTAGAGCTGGTACTGAAACTCCGTCCT
CAGGTCTTCAGTCCTGGGGATTACATTTGCCGCAAAGGGGACATCGGCAAGGAGAT
GTACATCATTAAGGAGGGCAAACTGGCAGTGGTGGCTGATGATGGTGTGACTCAGT
ATGCTCTGCTGTCGGCTGGAAGCTGCTTTGGCGAGATCAGTATCCTTAACATTAAGG
GCAGTAAAATGGGCAATCGACGCACAGCTAATATCCGCAGCCTGGGCTACTCAGAT
CTCTTCTGCTTGTCCAAGGATGATCTTATGGAAGCTGTGACTGAGTACCCTGATGCC
AAGAAAGTCCTAGAAGAGAGGGGTCGGGAGATCCTCATGAAGGAGGGACTGCTGG
ATGAGAACGAAGTGGCAACCAGCATGGAGGTCGACGTGCAGGAGAAGCTAGGGCA
GCTGGAGACCAACATGGAAACCTTGTACACTCGCTTTGGCCGCCTGCTGGCTGAGTA
CACGGGGGCCCAGCAGAAGCTCAAGCAGCGCATCACAGTTCTGGAAACCAAGATGA
AACAGAACAATGAAGATGACTACCTGTCTGATGGGATGAACAGCCCTGAGCTGGCT
GCTGCTGACGAGCCATAA
```

FIG. 2 hOCNC2

```
ATGAGCCAGGACACCAAAGTGAAGACAACAGAGTCCAGTCCCCCAGCCCCATCCAA
GGCCAGGAAGTTGCTGCCTGTCCTGGACCCATCTGGGGATTACTACTACTGGTGGCT
GAACACAATGGTCTTCCCAGTCATGTATAACCTCATCATCCTCGTGTGCAGAGCCTG
CTTCCCCGACTTGCAGCACGGTTATCTGGTGGCCTGGTTGGTGCTGGACTACACGAG
TGACCTGCTATACCTACTAGACATGGTGGTGCGCTTCCACACAGGATTCTTGGAACA
GGGCATCCTGGTGGTGGACAAGGGTAGGATCTCGAGTCGCTACGTTCGCACCTGGA
GTTTCTTCTTGGACCTGGCTTCCCTGATGCCCACAGATGTGGTCTACGTGTCGGCTGGG
CCCGCACACACCCACCCTGAGGCTGAACCGCTTTCTCCGCGCGCCCCGCCTCTTCGA
GGCCTTCGACCGCACAGAGACCCGCACAGCTTACCCAAATGCCTTTCGCATTGCCAA
GCTGATGCTTTACATTTTTGTCGTCATCCATTGGAACAGCTGCCTATACTTTGCCCTA
TCCCGGTACCTGGGCTTCGGGCGTGACGCATGGGTGTACCCGGACCCCGCGCAGCCT
GGCTTTGAGCGCCTGCGGCGCCAGTACCTCTATAGCTTTTACTTCTCCACGCTGATAC
TGACTACAGTGGGCGATACACCGCCGCCAGCCAGGGAAGAAGAGTACCTCTTCATG
GTGGGCGACTTCCTGCTGGCCGTCATGGGTTTCGCCACCATCATGGGTAGCATGAGC
TCTGTCATCTACAACATGAACACTGCAGATGCGGCTTTCTACCCAGATCATGCACTG
GTGAAGAAGTACATGAAGCTGCAGCACGTCAACCGCAAGCTGGAGCGGCGAGTTAT
TGACTGGTATCAGCACCTGCAGATCAACAAGAAGATGACCAACGAGGTAGCCATCT
TACAGCACTTGCCTGAGCGGCTGCGGGCAGAAGTGGCTGTGCTGTGCACCTGTCCA
CTCTGAGCCGGGTGCAGATCTTTCAGAACTGTGAGGCCAGCCTGCTGGAGGAGCTG
GTGCTAAGCTGCCAGCCCCAGACCTACTCACCAGGTGAATATGTATGCCGCAAAGG
AGACATTGGCCAAGAGATGTACATCATCCGAGAGGGTCAACTGGCCGTGGTGGCAG
ATGATGGTATCACACAGTATGCTGTGCTCGGTGCAGGGCTCTACTTTGGGGAGATCA
GCATCATCAACATCAAAGGGAACATGTCTGGGAACCGCCGCACAGCCAACATCAAG
AGCCTAGGTTATTCAGACCTATTCTGCCTGAGCAAGGAGGACCTGCGGGAGGTGCTG
AGCGAGTATCCACAAGCACAGACCATCATGGAGGAGAAAGGACGTGAGATCCTGCT
GAAAATGAACAAGTTGGACGTGAATGCTGAGGCAGCTGAGATCGCCCTGCCAGGAGG
CCACAGAGTCCCGGCTACGAGGCCTAGACCAGCAGCTGGATGATCTACAGACCAAG
TTTGCTCGCCTCCTGGCTGAGCTGGAGTCCAGCGCACTTAAGATTGCTTACCGCATT
GAACGGCTGGAGTGGCAGACTCGAGAGTGGCCAATGCCCGAGGACCTGGCTGAGGC
TGATGACGAGGGTGAGCCTGAGGAGGGAACTTCCAAAGATGAAGAGGGCAGGGCC
AGCCAGGAGGGACCCCCAGGTCCAGAGTGA
```

FIG. 3 hB1B

```
ATGGCTACACCATGTCAGAACATGGAGCTGAATCGCCTAGTCCAGGACCAGATACCTGGCC
AGGTGGCCTCTGCCTCTGCCCTCCAAAACCTGGTAGAGCATCTCCCTAATGTGCCCAGCTAC
CGCATCCCAATCACCCGCATCCCTGTCCTCACCTCCCGGAGAACCAGCTTGTCCAACTCCAG
CTTCGCCAAGGAGACCAGGAGCTCCATCCGCCAACTAGTGCCTGCCACGAAACAGCACCCA
GAAGTGCAGGTGGAAGATACTGATGCTGATAGCTGCCCCCTCATGGCAGAAGAGAATCCAC
CCTCAACCGTGTTGCCGCCACCGTCTCCTGCCAAATCAGACACCCTTATAGTCCCAAGCTCA
GCCTCGGGGACACACAGGAAGAAGCTGCCCTCTGAGGATGATGAGGCTGAAGAGCTCAAGG
CGTTGTCACCAGCAGAGTCCCCAGTGGTTGCCTGGTCTGACCCCACCACCCCGAAGGACACT
GATGGCCAGGACCGTGCGGCCTCCACGGCCAGCACAAATAGCGCCATCATCAACGACCGGC
TCCAGGAGCTGGTGAAGCTCTTCAAGGAGCGGACAGAGAAAGTGAAGGAGAAACTCATTGA
CCCTGACGTCACCTCTGATGAGGAGAGCCCCAAGCCCTCCCCAGCCAAGAAAGCCCCAGAG
CCAGCTCCAGACACAAAGCCCGCTGAAGCCGAGCCAGTGGAAGAGGAGCACTATTGCGACA
TGCTCTGCTGCAAGTTCAAACACCGCCCCTGGAAGAAGTACCAGTTTCCCCAGAGCATTGAC
CCGCTGACCAACCTGATGTATGTCCTATGGCTGTTCTTCGTGGTGATGGCCTGGAATTGGAA
CTGTTGGCTGATTCCCGTGCGCTGGGCCTTCCCCTACCAGACCCCGGACAACATCCACCACT
GGCTGCTGATGGATTACCTATGCGACCTCATCTACTTCCTGGACATCACCGTGTTCCAGACAC
GCCTGCAGTTTGTCAGAGGCGGGGACATCATTACGGACAAAAAGGACATGCGAAATAACTA
CCTGAAGTCTCGCCGCTTCAAGATGGACCTGCTCAGCCTCCTGCCCTTGGATTTTCTCTATTT
GAAAGTCGGTGTGAACCCCCTCCTCCGCCTGCCCCGCTGTTTAAAGTACATGGCCTTCTTCGA
GTTTAACAGCCGCCTGGAATCCATCCTCAGCAAAGCCTACGTGTACAGGGTCATCAGGACCA
CAGCCTACCTTCTCTACAGCCTGCATTTGAATTCCTGTCTTTATTACTGGGCATCGGCCTATC
AGGGCCTCGGCTCCACTCACTGGGTTTACGATGGCGTGGGAAACAGTTATATTCGCTGTTAC
TACTTTGCTGTGAAGACCCTCATCACCATCGGGGGGCTGCCTGACCCCAAGACACTCTTTGA
AATTGTCTTCCAGCTGCTGAATTATTTCACGGGCGTCTTTGCTTTCTCTGTGATGATCGGACA
GATGAGAGATGTGGTAGGGGCCGCCACCGCGGGACAGACCTACTACCGCAGCTGCATGGAC
AGCACGGTGAAGTACATGAATTTCTACAAGATCCCCAAGTCCGTGCAGAACCGCGTCAAGA
CCTGGTACGAGTACACCTGGCACTCGCAAGGCATGCTGGATGAGTCAGAGCTGATGGTGCA
GCTTCCAGACAAGATGCGGCTGGACCTCGCCATCGACGTGAACTACAACATCGTTAGCAAA
GTCGCACTCTTTCAGGGCTGTGACCGGCAGATGATCTTTGACATGCTGAAGAGGCTTCGCTC
TGTTGTCTACCTGCCCAACGACTATCTGTGCAAGAAGGGGGAGATCGGCCGTGAGATGTACA
TCATCCAGGCAGGGCAAGTGCAGGTCTTGGGCGGCCCTGATGGGAAATCTGTGCTGGTGAC
GCTGAAAGCTGGATCTGTGTTTGGAGAAATAAGCTTGCTGGCTGTTGGGGGCGGGAACCGG
CGCACGGCCAACGTGGTGGCGCACGGGTTTACCAACCTCTTCATCCTGGATAAGAAGGACCT
GAATGAGATTTTGGTGCATTATCCTGAGTCTCAGAAGTTACTCCGGAAGAAAGCCAGGCGCA
TGCTGAGAAGCAACAATAAGCCCAAGGAGGAGAAGAGCGTGCTGATCCTTCCACCCCGGGC
GGGCACCCCAAAGCTCTTCAACGCTGCCCTCGCTATGACAGGAAAGATGGGTGGCAAGGGG
GCAAAAGGCGGCAAACTTGCTCACCTCCGGGCCCGGCTCAAAGAACTGGCCGCGCTGGAGG
CGGCTGCAAAGCAGCAAGAGTTGGTGGAACAGGCCAAGAGCTCGCAAGACGTCAAGGGAG
AGGAAGGCTCCGCCGCCCCAGACCAGCACACGCACCCAAAGGAGGCCGCCACCGACCCACC
CGCGCCCCGGACGCCCCCCGAGCCCCCGGGGTCTCCACCGAGCTCTCCACCGCCTGCCTCCC
TTGGGAGGCCGGAGGGAGAGGAGGAGGGGCCGGCCGAGCCCGAAGAGCACTCGGTGAGGA
TCTGCATGAGCCCGGGCCCGGAGCCGGGAGAGCAGATCCTGTCGGTGAAGATGCCGGAGGA
AAGGGAGGAGAAGGCGGAGTAA
```

FIG. 4

SEQUENCE LISTING

```
<160> NUMBER OF SEQ ID NOS: 12

<210> SEQ ID NO 1
<211> LENGTH: 1995
<212> TYPE: DNA
<213> ORGANISM: Homo sapiens

<400> SEQUENCE: 1
atgaccgaaa aaaccaatgg tgtgaagagc tccccagcca ataatcacaa ccatcatgca      60
cctcctgcca tcaaggccaa tggcaaagat gaccacagga caagcagcag gccacactct     120
gcagctgacg atgacacctc ctcagaactg cagaggctgg cagacgtgga tgccccacag     180
cagggaagga gtggcttccg caggatagtt cgcctggtgg ggatcatcag agaatgggcc     240
aacaagaatt tccgagagga ggaacctagg cctgactcat tcctcgagcg ttttcgtggg     300
cctgaactcc agactgtgac cacacaggag ggggatggca aaggcgacaa ggatggcgag     360
gacaaaggca ccaagaagaa atttgaacta tttgtcttgg acccagctgg ggattggtac     420
tactgctggc tatttgtcat tgccatgccc gtcctttaca actggtgcct gctggtggcc     480
agagcctgct tcagtgacct acagaaaggc tactacctgg tgtggctggt gctggattat     540
gtctcagatg tggtctacat tgcggacctc ttcatccgat tgcgcacagg tttcctggag     600
caggggctgc tggtcaaaga taccaagaaa ctgcgagaca actacatcca caccctgcag     660
ttcaagctgg atgtggcttc catcatcccc actgacctga tctatttttgc tgtggacatc     720 cacagccctg aggtgcgctt caaccgcctg ctgcactttg cccgcatgtt tgagttcttt     780
gaccggacag agacacgcac caactaccct aacatcttcc gcatcagcaa ccttgtcctc     840
tacatcttgg tcatcatcca ctggaatgcc tgcatctatt atgccatctc caaatccata     900
```

```
ggctttgggg tcgacacctg ggtttaccca aacatcactg accctgagta tggctacctg    960
gctagggaat acatctattg cctttactgg tccacactga ctctcactac cattggggag   1020
acaccacccc ctgtaaagga tgaggagtac ctatttgtca tctttgactt cctgattggc   1080
gtcctcatct ttgccaccat cgtgggaaat gtgggctcca tgatctccaa catgaatgcc   1140
acccgggcag agttccaggc taagatcgat gccgtgaaac actacatgca gttccgaaag   1200
gtcagcaagg ggatggaagc caaggtcatt aggtggtttg actacttgtg gaccaataag   1260
aagacagtgg atgagcgaga aattctcaag aatctgccag ccaagctcag ggctgagata   1320
gccatcaatg tccacttgtc cacactcaag aaagtgcgca tcttccatga ttgtgaggct   1380
ggcctgctgg tagagctggt actgaaactc cgtcctcagg tcttcagtcc tggggattac   1440
atttgccgca aggggacat cggcaaggag atgtacatca ttaaggaggg caaactggca   1500
gtggtggctg atgatggtgt gactcagtat gctctgctgt cggctggaag ctgctttggc   1560
gagatcagta tccttaacat taagggcagt aaaatgggca atcgacgcac agctaatatc   1620
cgcagcctgg gctactcaga tctcttctgc ttgtccaagg atgatcttat ggaagctgtg   1680
actgagtacc ctgatgccaa gaaagtccta aagagagggg tcgggagat cctcatgaag   1740 gagggactgc tggatgagaa cgaagtggca accagcatgg aggtcgacgt gcaggagaag   1800
ctagggcagc tggagaccaa catggaaacc ttgtacactc gctttggccg cctgctggct   1860
gagtacacgg ggcccagca gaagctcaag cagcgcatca cagttctgga aaccaagatg   1920
aaacagaaca atgaagatga ctacctgtct gatgggatga cagccctga gctggctgct   1980 gctgacgagc cataa                                                    1995

<210> SEQ ID NO 2
<211> LENGTH: 1728
<212> TYPE: DNA
<213> ORGANISM: Homo sapiens

<400> SEQUENCE: 2
atgagccagg acaccaaagt gaagacaaca gagtccagtc ccccagcccc atccaaggcc    60
aggaagttgc tgcctgtcct ggacccatct ggggattact actactggtg gctgaacaca   120
atggtcttcc cagtcatgta taacctcatc atcctcgtgt gcagagcctg cttccccgac   180
ttgcagcacg gttatctggt ggcctggttg gtgctggact acacgagtga cctgctatac   240
ctactagaca tggtggtgcg cttccacaca ggattcttgg aacagggcat cctggtggtg   300
gacaagggta ggatctcgag tcgctacgtt cgcacctgga gtttcttctt ggacctggct   360
tccctgatgc ccacagatgt ggtctacgtg cggctgggcc gcacacacc cacccctgagg   420 ctgaaccgct ttctccgcgc gccccgcctc ttcgaggcct cgaccgcac agagacccgc   480 acagcttacc caaatgcctt tcgcattgcc aagctgatgc tttacatttt tgtcgtcatc   540
cattggaaca gctgcctata ctttgcccta tcccggtacc tgggcttcgg gcgtgacgca   600
tgggtgtacc cggacccgc gcagcctggc tttgagcgcc tcggcgccca gtacctctat   660 agctttact tctccacgct gatactgact acagtgggcg atacaccgcc gccagccagg   720
gaagaagagt acctcttcat ggtgggcgac ttcctgctgg ccgtcatggg tttcgccacc   780
atcatgggta gcatgagctc tgtcatctac aacatgaaca ctgcagatgc ggctttctac   840
ccagatcatg cactggtgaa gaagtacatg aagctgcagc acgtcaaccg caagctggag   900
cggcgagtta ttgactggta tcagcacctg cagatcaaca agaagatgac caacgaggta   960
gccatcttac agcacttgcc tgagcggctg cgggcagaag tggctgtgtc tgtgcacctg  1020
```

```
tccactctga gccgggtgca gatctttcag aactgtgagg ccagcctgct ggaggagctg    1080
gtgctgaagc tgcagcccca gacctactca ccaggtgaat atgtatgccg caaggagac    1140 attggccaag agatgtacat catccgagag ggtcaactgg ccgtggtggc agatgatggt    1200
atcacacagt atgctgtgct cggtgcaggg ctctactttg gggagatcag catcatcaac    1260
atcaaaggga acatgtctgg gaaccgccgc acagccaaca tcaagagcct aggttattca    1320
gacctattct gcctgagcaa ggaggacctg cgggaggtgc tgagcgagta tccacaagca    1380
cagaccatca tggaggagaa aggacgtgag atcctgctga aaatgaacaa gttggacgtg    1440
aatgctgagg cagctgagat cgccctgcag gaggccacag agtcccggct acgaggccta    1500
gaccagcagc tggatgatct acagaccaag tttgctcgcc tcctggctga gctggagtcc    1560
agcgcactta agattgctta ccgcattgaa cggctggagt ggcagactcg agagtggcca    1620
atgcccgagg acctggctga ggctgatgac gagggtgagc ctgaggaggg aacttccaaa    1680
gatgaagagg gcagggccag ccaggaggga cccccaggtc cagagtga               1728

<210> SEQ ID NO 3
<211> LENGTH: 2607
<212> TYPE: DNA
<213> ORGANISM: Homo sapiens

<400> SEQUENCE: 3
atggctacac catgtcagaa catggagctg aatcgcctag tccaggacca gatacctggc      60
caggtggcct ctgcctctgc cctccaaaac ctggtagagc atctccctaa tgtgcccagc     120
taccgcatcc caatcacccg catccctgtc ctcacctccc ggagaaccag cttgtccaac     180
tccagcttcg ccaaggagac caggagctcc atccgccaac tagtgcctgc cacgaaacag     240
cacccagaag tgcaggtgga agatactgat gctgatagct gcccctcat ggcagaagag      300 aatccaccct caaccgtgtt gccgccaccg tctcctgcca aatcagacac ccttatagtc     360
ccaagctcag cctcggggac acacaggaag aagctgccct ctgaggatga tgaggctgaa     420
gagctcaagg cgttgtcacc agcagagtcc ccagtggttg cctggtctga ccccaccacc     480
ccgaaggaca ctgatggcca ggaccgtgcg gcctccacgg ccagcacaaa tagcgccatc     540
atcaacgacc ggctccagga gctggtgaag ctcttcaagg agcggacaga gaaagtgaag     600
gagaaactca ttgaccctga cgtcacctct gatgaggaga gccccaagcc ctccccagcc     660
aagaaagccc cagagccagc tccagacaca aagcccgctg aagccgagcc agtggaagag     720
gagcactatt gcgacatgct ctgctgcaag ttcaaacacc gcccctggaa gaagtaccag     780
tttccccaga gcattgaccc gctgaccaac ctgatgtatg tcctatggct gttcttcgtg     840
gtgatggcct ggaattggaa ctgttggctg attcccgtgc gctgggcctt ccctaccag     900 accccggaca catccaccca ctggctgctg atggattacc tatgcgacct catctacttc    960
ctggacatca ccgtgttcca gacacgcctg cagtttgtca gaggcgggga catcattacg   1020
gacaaaaagg acatgcgaaa taactacctg aagtctcgcc gcttcaagat ggacctgctc   1080
agcctcctgc ccttggattt tctctatttg aaagtcggtg tgaacccct cctccgcctg   1140 ccccgctgtt taaagtacat ggccttcttc gagtttaaca gccgcctgga atccatcctc   1200
agcaaagcct acgtgtacag ggtcatcagg accacagcct accttctcta cagcctgcat   1260
ttgaattcct gtcttttatta ctgggcatcg gcctatcagg gcctcggctc cactcactgg   1320
gtttacgatg gcgtgggaaa cagttatatt cgctgttact actttgctgt gaagaccctc   1380
atcaccatcg gggggctgcc tgaccccaag acactctttg aaattgtctt ccagctgctg   1440
```

```
aattatttca cgggcgtctt tgctttctct gtgatgatcg gacagatgag agatgtggta    1500
ggggccgcca ccgcgggaca gacctactac cgcagctgca tggacagcac ggtgaagtac    1560
atgaatttct acaagatccc caagtccgtg cagaaccgcg tcaagacctg gtacgagtac    1620
acctggcact cgcaaggcat gctggatgag tcagagctga tggtgcagct tccagacaag    1680
atgcggctgg acctcgccat cgacgtgaac tacaacatcg ttagcaaagt cgcactcttt    1740
cagggctgtg accggcagat gatctttgac atgctgaaga ggcttcgctc tgttgtctac    1800
ctgcccaacg actatgtgtg caagaagggg agatcggcc gtgagatgta catcatccag    1860
gcagggcaag tgcaggtctt gggcggccct gatgggaaat ctgtgctggt gacgctgaaa    1920
gctggatctg tgtttggaga ataagcttg ctggctgttg ggggcgggaa ccggcgcacg    1980
gccaacgtgg tggcgcacgg gtttaccaac ctcttcatcc tggataagaa ggacctgaat    2040
gagattttgg tgcattatcc tgagtctcag aagttactcc ggaagaaagc caggcgcatg    2100
ctgagaagca acaataagcc caaggaggag aagagcgtgc tgatccttcc accccgggcg    2160
ggcaccccaa agctcttcaa cgctgccctc gctatgacag gaaagatggg tggcaagggg    2220
gcaaaaggcg gcaaacttgc tcacctccgg gcccggctca agaactggc cgcgctggag    2280 gcggctgcaa agcagcaaga gttggtggaa caggccaaga gctcgcaaga cgtcaaggga    2340
gaggaaggct ccgccgcccc agaccagcac acgcacccaa aggaggccgc caccgaccca    2400
cccgcgcccc ggacgccccc cgagcccccg gggtctccac cgagctctcc accgcctgcc    2460
tcccttggga ggccggaggg agaggaggag gggccggccg agcccgaaga gcactcggtg    2520
aggatctgca tgagcccggg cccggagccg ggagagcaga tcctgtcggt gaagatgccg    2580
gaggaaaggg aggagaaggc ggagtaa                                        2607
```

<210> SEQ ID NO 4
<211> LENGTH: 1995
<212> TYPE: DNA
<213> ORGANISM: Homo sapiens

<400> SEQUENCE: 4

```
atgaccgaaa aaccaatgg tgtgaagagc tccccagcca ataatcacaa ccatcatgca      60
cctcctgcca tcaaggccaa tggcaaagat gaccacagga caagcagcag gccacactct    120
gcagctgacg atgacaccct ctcagaactg cagaggctgg cagacgtgga tgccccacag    180
cagggaagga gtggcttccg caggatagtt cgcctggtgg ggatcatcag agaatgggcc    240
aacaagaatt tccgagagga ggaacctagg cctgactcat tcctcgagcg ttttcgtggg    300
cctgaactcc agactgtgac cacacaggag ggggatggca aaggcgacaa ggatggcgag    360
gacaaaggca ccaagaagaa atttgaacta tttgtcttgg acccagctgg ggattggtac    420
tactgctggc tatttgtcat tgccatgccc gtccttttaca actggtgcct gctggtggcc    480
agagcctgct tcagtgacct acagaaaggc tactacctgg tgtggctggt gctggattat    540
gtctcagatg tggtctacat tgcggacctc ttcatccgat tgcgcacagg tttcctggag    600
caggggctgc tggtcaaaga taccaagaaa ctgcagacaa actacatcca caccctgcag    660
ttcaagctgg atgtgccttc catcatcccc actgacctga tctattttgc tgtggacatc    720
cacagccctg aggtgcgctt caaccgcctg ctgcactttg cccgcatgtt tgagttcttt    780
gaccggacag agacacgcac caactaccct aacatcttcc gcatcagcaa ccttgtcctc    840
tacatcttgg tcatcatcca ctggaatgcc tgcatctatt atgccatctc caatcca      900 ggctttgggg tcgacaccctg ggtttaccca aacatcactg accctgagta tggctacctg    960
```

-continued

```
gctagggaat acatctattg cctttactgg tccacactga ctctcactac cattggggag   1020
acaccacccc ctgtaaagga tgaggagtac ctatttgtca tctttgactt cctgattggc   1080
gtcctcatct ttgccaccat cgtgggaaat gtgggctcca tgatctccaa catgaatgcc   1140
acccgggcag agttccaggc taagatcgat gccgtgaaac actacatgca gttccgaaag   1200
gtcagcaagg ggatggaagc caaggtcatt aggtggtttg actacttgtg gaccaataag   1260
aagacagtgg atgagcgaga aattctcaag aatctgccag ccaagctcag ggctgagata   1320
gccatcaatg tccacttgtc cacactcaag aaagtgcgca tcttccatga ttgggaggct   1380
ggcctgctgg tagagctggt actgaaactc cgtcctcagg tcttcagtcc tggggattac   1440
atttgccgca aggggacat cggcaaggag atgtacatca ttaaggaggg caaactggca   1500
gtggtggctg atgatggtgt gactcagtat gctctgctgt cggctggaag ctgctttggc   1560
gagatcagta tccttaacat taagggcagt aaaatgggca atcgacgcac agctaatatc   1620
cgcagcctgg gctactcaga tctcttctgc ttgtccaagg atgatcttat ggaagctgtg   1680
actgagtacc ctgatgccaa gaaagtccta gaagagaggg tcgggagat cctcatgaag   1740 atgggactgc tggatgagaa cgaagtggca accagcatgg aggtcgacgt gcaggagaag   1800
ctagggcagc tggagaccaa catggaaacc ttgtacactc gctttggccg cctgctggct   1860
gagtacacgg gggcccagca gaagctcaag cagcgcatca cagttctgga aaccaagatg   1920
aaacagaaca atgaagatga ctacctgtct gatgggatga acagccctga gctggctgct   1980
gctgacgagc cataa                                                    1995
```

<210> SEQ ID NO 5
<211> LENGTH: 239
<212> TYPE: PRT
<213> ORGANISM: Rattus sp.

<400> SEQUENCE: 5

```
Asp Glu Glu Tyr Leu Phe Val Ile Phe Asp Phe Leu Ile Gly Val Leu
  1               5                  10                  15

Ile Phe Ala Thr Ile Val Gly Asn Val Gly Ser Met Ile Ser Asn Met
             20                  25                  30

Asn Ala Thr Arg Ala Glu Phe Gln Ala Lys Ile Asp Ala Val Lys His
         35                  40                  45

Tyr Met Gln Phe Arg Lys Val Ser Lys Asp Met Glu Ala Lys Val Ile
     50                  55                  60

Lys Trp Phe Asp Tyr Leu Trp Thr Asn Lys Thr Val Asp Glu Arg
 65                  70                  75                  80

Glu Val Leu Lys Asn Leu Pro Ala Lys Leu Arg Ala Glu Ile Ala Ile
                 85                  90                  95

Asn Val His Leu Ser Thr Leu Lys Lys Val Arg Ile Phe Gln Asp Cys
            100                 105                 110

Glu Ala Gly Leu Leu Val Glu Leu Val Leu Lys Leu Arg Pro Gln Val
        115                 120                 125

Phe Ser Pro Gly Asp Tyr Ile Cys Arg Lys Gly Asp Ile Gly Lys Glu
    130                 135                 140

Met Tyr Ile Ile Lys Glu Gly Lys Leu Ala Val Val Ala Asp Asp Gly
145                 150                 155                 160

Val Thr Gln Tyr Ala Leu Leu Ser Ala Gly Ser Cys Phe Gly Glu Ile
                165                 170                 175

Ser Ile Leu Asn Ile Lys Gly Ser Lys Met Gly Asn Arg Arg Thr Ala
            180                 185                 190
```

```
Asn Ile Arg Ser Leu Gly Tyr Ser Asp Leu Phe Cys Leu Ser Lys Asp
        195                 200                 205

Asp Leu Met Glu Ala Val Thr Glu Tyr Pro Asp Ala Lys Lys Val Leu
    210                 215                 220

Glu Glu Arg Gly Arg Glu Ile Leu Met Lys Gly Leu Leu Asp
225                 230                 235

<210> SEQ ID NO 6
<211> LENGTH: 239
<212> TYPE: PRT
<213> ORGANISM: Rattus sp.

<400> SEQUENCE: 6

Glu Glu Glu Tyr Leu Phe Met Val Gly Asp Phe Leu Leu Ala Val Met
1               5                   10                  15

Gly Phe Ala Thr Ile Met Gly Ser Met Ser Ser Val Ile Tyr Asn Met
            20                  25                  30

Asn Thr Ala Asp Ala Ala Phe Tyr Pro Asp His Ala Leu Val Lys Lys
            35                  40                  45

Tyr Met Lys Leu Gln His Val Asn Lys Arg Leu Glu Arg Arg Val Ile
        50                  55                  60

Asp Trp Tyr Gln His Leu Gln Ile Asn Lys Lys Met Thr Asn Glu Val
65                  70                  75                  80

Ala Ile Leu Gln His Leu Pro Glu Arg Leu Arg Ala Glu Val Ala Val
                85                  90                  95

Ser Val His Leu Ser Thr Leu Ser Arg Val Gln Ile Phe Gln Asn Cys
            100                 105                 110

Glu Ala Ser Leu Leu Glu Glu Leu Val Leu Lys Leu Gln Pro Gln Thr
        115                 120                 125

Tyr Ser Pro Gly Glu Tyr Val Cys Arg Lys Gly Asp Ile Gly Arg Glu
    130                 135                 140

Met Tyr Ile Ile Arg Glu Gly Gln Leu Ala Val Val Ala Asp Asp Gly
145                 150                 155                 160

Val Thr Gln Tyr Ala Val Leu Gly Ala Gly Leu Tyr Phe Gly Glu Ile
                165                 170                 175

Ser Ile Ile Asn Ile Lys Gly Asn Met Ser Gly Asn Arg Arg Thr Ala
            180                 185                 190

Asn Ile Lys Ser Leu Gly Tyr Ser Asp Leu Phe Cys Leu Ser Lys Glu
        195                 200                 205

Asp Leu Arg Glu Val Leu Ser Glu Tyr Pro Gln Ala Gln Ala Val Met
    210                 215                 220

Glu Glu Lys Gly Arg Glu Ile Leu Leu Lys Met Asn Lys Leu Asp
225                 230                 235

<210> SEQ ID NO 7
<211> LENGTH: 237
<212> TYPE: PRT
<213> ORGANISM: Rattus sp.

<400> SEQUENCE: 7

Leu Phe Glu Ile Val Phe Gln Leu Leu Asn Tyr Phe Thr Gly Val Phe
1               5                   10                  15

Ala Phe Ser Val Met Ile Gly Gln Met Arg Asp Val Val Gly Ala Ala
            20                  25                  30

Thr Ala Gly Gln Thr Tyr Arg Ser Cys Met Asp Ser Thr Val Lys
        35                  40                  45
```

```
Tyr Met Asn Phe Tyr Lys Ile Pro Arg Ser Val Gln Asn Arg Val Lys
             50                  55                  60

Thr Trp Tyr Glu Tyr Thr Trp His Ser Gln Gly Met Leu Asp Glu Ser
 65                  70                  75                  80

Glu Leu Met Val Gln Leu Pro Asp Lys Met Arg Leu Asp Leu Ala Ile
                 85                  90                  95

Asp Val Asn Tyr Asn Ile Val Ser Lys Val Ala Leu Phe Gln Gly Cys
                100                 105                 110

Asp Arg Gln Met Ile Phe Asp Met Leu Lys Arg Leu Arg Ser Val Val
            115                 120                 125

Tyr Leu Pro Asn Asp Tyr Val Cys Lys Lys Gly Glu Ile Gly Arg Glu
        130                 135                 140

Met Tyr Ile Ile Gln Ala Gly Gln Val Gln Val Leu Gly Gly Pro Asp
145                 150                 155                 160

Gly Lys Ala Val Leu Val Thr Leu Lys Ala Gly Ser Val Phe Gly Glu
                165                 170                 175

Ile Ser Leu Leu Ala Val Gly Gly Gly Asn Arg Arg Thr Ala Asn Val
                180                 185                 190

Val Ala His Gly Phe Thr Asn Leu Phe Ile Leu Asp Lys Lys Asp Leu
            195                 200                 205

Asn Glu Ile Leu Val His Tyr Pro Glu Ser Gln Lys Leu Leu Arg Lys
        210                 215                 220

Lys Ala Arg Arg Met Leu Arg Asn Asn Asn Lys Pro Lys
225                 230                 235

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      linker sequence

<400> SEQUENCE: 8
ggcgcgccgc catg                                                        14

<210> SEQ ID NO 9
<211> LENGTH: 239
<212> TYPE: PRT
<213> ORGANISM: Homo sapiens

<400> SEQUENCE: 9

Asp Glu Glu Tyr Leu Phe Val Ile Phe Asp Phe Leu Ile Gly Val Leu
  1               5                  10                  15

Ile Phe Ala Thr Ile Val Gly Asn Val Gly Ser Met Ile Ser Asn Met
                 20                  25                  30

Asn Ala Thr Arg Ala Glu Phe Gln Ala Lys Ile Asp Ala Val Lys His
             35                  40                  45

Tyr Met Gln Phe Arg Lys Val Ser Lys Gly Met Glu Ala Lys Val Ile
         50                  55                  60

Arg Trp Phe Asp Tyr Leu Trp Thr Asn Lys Lys Thr Val Asp Glu Arg
 65                  70                  75                  80

Glu Ile Leu Lys Asn Leu Pro Ala Lys Leu Arg Ala Glu Ile Ala Ile
                 85                  90                  95

Asn Val His Leu Ser Thr Leu Lys Lys Val Arg Ile Phe His Asp Cys
                100                 105                 110

Glu Ala Gly Leu Leu Val Glu Leu Val Leu Lys Leu Arg Pro Gln Val
            115                 120                 125
```

```
Phe Ser Pro Gly Asp Tyr Ile Cys Arg Lys Gly Asp Ile Gly Lys Glu
    130                 135                 140

Met Tyr Ile Ile Lys Glu Gly Lys Leu Ala Val Val Ala Asp Asp Gly
145                 150                 155                 160

Val Thr Gln Tyr Ala Leu Leu Ser Ala Gly Ser Cys Phe Gly Glu Ile
                165                 170                 175

Ser Ile Leu Asn Ile Lys Gly Ser Lys Met Gly Asn Arg Arg Thr Ala
                180                 185                 190

Asn Ile Arg Ser Leu Gly Tyr Ser Asp Leu Phe Cys Leu Ser Lys Asp
            195                 200                 205

Asp Leu Met Glu Ala Val Thr Glu Tyr Pro Asp Ala Lys Lys Val Leu
    210                 215                 220

Glu Glu Arg Gly Arg Glu Ile Leu Met Lys Gly Leu Leu Asp
225                 230                 235

<210> SEQ ID NO 10
<211> LENGTH: 239
<212> TYPE: PRT
<213> ORGANISM: Homo sapiens

<400> SEQUENCE: 10

Glu Glu Glu Tyr Leu Phe Met Val Gly Asp Phe Leu Leu Ala Val Met
1               5                   10                  15

Gly Phe Ala Thr Ile Met Gly Ser Met Ser Ser Val Ile Tyr Asn Met
                20                  25                  30

Asn Thr Ala Asp Ala Ala Phe Tyr Pro Asp His Ala Leu Val Lys Lys
            35                  40                  45

Tyr Met Lys Leu Gln His Val Asn Arg Lys Leu Glu Arg Arg Val Ile
    50                  55                  60

Asp Trp Tyr Gln His Leu Gln Ile Asn Lys Lys Met Thr Asn Glu Val
65                  70                  75                  80

Ala Ile Leu Gln His Leu Pro Glu Arg Leu Arg Ala Glu Val Glu Val
                85                  90                  95

Ser Val His Leu Ser Thr Leu Ser Arg Val Gln Ile Phe Gln Asn Cys
                100                 105                 110

Glu Ala Ser Leu Leu Glu Glu Leu Val Leu Lys Leu Gln Pro Gln Thr
            115                 120                 125

Tyr Ser Pro Gly Glu Tyr Val Cys Arg Lys Gly Asp Ile Gly Gln Glu
    130                 135                 140

Met Tyr Ile Ile Arg Glu Gly Gln Leu Ala Val Val Ala Asp Asp Gly
145                 150                 155                 160

Ile Thr Gln Tyr Ala Val Leu Gly Ala Gly Leu Tyr Phe Gly Glu Ile
                165                 170                 175

Ser Ile Ile Asn Ile Lys Gly Asn Met Ser Gly Asn Arg Arg Thr Ala
                180                 185                 190

Asn Ile Lys Ser Leu Gly Tyr Ser Asp Leu Phe Cys Leu Ser Lys Glu
            195                 200                 205

Asp Leu Arg Glu Val Leu Ser Glu Tyr Pro Gln Ala Gln Thr Ile Met
    210                 215                 220

Glu Glu Lys Gly Arg Glu Ile Leu Leu Lys Met Asn Lys Leu Asp
225                 230                 235

<210> SEQ ID NO 11
<211> LENGTH: 237
<212> TYPE: PRT
<213> ORGANISM: Homo sapiens
```

<400> SEQUENCE: 11

Leu Phe Glu Ile Val Phe Gln Leu Leu Asn Tyr Phe Thr Gly Val Phe
1               5                   10                  15

Ala Phe Ser Val Met Ile Gly Gln Met Arg Asp Val Val Gly Ala Ala
            20                  25                  30

Thr Ala Gly Gln Thr Tyr Tyr Arg Ser Cys Met Asp Ser Thr Val Lys
        35                  40                  45

Tyr Met Asn Phe Tyr Lys Ile Pro Lys Ser Val Gln Asn Arg Val Lys
    50                  55                  60

Thr Trp Tyr Glu Tyr Thr Trp His Ser Gln Gly Met Leu Asp Glu Ser
65                  70                  75                  80

Glu Leu Met Val Gln Leu Pro Asp Lys Met Arg Leu Asp Leu Ala Ile
            85                  90                  95

Asp Val Asn Tyr Asn Ile Val Ser Lys Val Ala Leu Phe Gln Gly Cys
        100                 105                 110

Asp Arg Gln Met Ile Phe Asp Met Leu Lys Arg Leu Arg Ser Val Val
    115                 120                 125

Tyr Leu Pro Asn Asp Tyr Val Cys Lys Lys Gly Glu Ile Gly Arg Glu
130                 135                 140

Met Tyr Ile Ile Gln Ala Gly Gln Val Gln Leu Gly Gly Pro Asp
145                 150                 155                 160

Gly Lys Ser Val Leu Val Thr Leu Lys Ala Gly Ser Val Phe Gly Glu
            165                 170                 175

Ile Ser Leu Leu Ala Val Gly Gly Gly Asn Arg Arg Thr Ala Asn Val
        180                 185                 190

Val Ala His Gly Phe Thr Asn Leu Phe Ile Leu Asp Lys Lys Asp Leu
    195                 200                 205

Asn Glu Ile Leu Val His Tyr Pro Glu Ser Gln Lys Leu Leu Arg Lys
210                 215                 220

Lys Ala Arg Arg Met Leu Arg Ser Asn Asn Lys Pro Lys
225                 230                 235

<210> SEQ ID NO 12
<211> LENGTH: 239
<212> TYPE: PRT
<213> ORGANISM: Homo sapiens

<400> SEQUENCE: 12

Asp Glu Glu Tyr Leu Phe Val Ile Phe Asp Phe Leu Ile Gly Val Leu
1               5                   10                  15

Ile Phe Ala Thr Ile Val Gly Asn Val Gly Ser Met Ile Ser Asn Met
            20                  25                  30

Asn Ala Thr Arg Ala Glu Phe Gln Ala Lys Ile Asp Ala Val Lys His
        35                  40                  45

Tyr Met Gln Phe Arg Lys Val Ser Lys Gly Met Glu Ala Lys Val Ile
    50                  55                  60

Arg Trp Phe Asp Tyr Leu Trp Thr Asn Lys Lys Thr Val Asp Glu Arg
65                  70                  75                  80

Glu Ile Leu Lys Asn Leu Pro Ala Lys Leu Arg Ala Glu Ile Ala Ile
            85                  90                  95

Asn Val His Leu Ser Thr Leu Lys Lys Val Arg Ile Phe His Asp Trp
        100                 105                 110

Glu Ala Gly Leu Leu Val Glu Leu Val Leu Lys Leu Arg Pro Gln Val
    115                 120                 125

-continued

```
Phe Ser Pro Gly Asp Tyr Ile Cys Arg Lys Gly Asp Ile Gly Lys Glu
    130                 135                 140

Met Tyr Ile Ile Lys Glu Gly Lys Leu Ala Val Val Ala Asp Asp Gly
145                 150                 155                 160

Val Thr Gln Tyr Ala Leu Leu Ser Ala Gly Ser Cys Phe Gly Glu Ile
                165                 170                 175

Ser Ile Leu Asn Ile Lys Gly Ser Lys Met Gly Asn Arg Arg Thr Ala
                180                 185                 190

Asn Ile Arg Ser Leu Gly Tyr Ser Asp Leu Phe Cys Leu Ser Lys Asp
            195                 200                 205

Asp Leu Met Glu Ala Val Thr Glu Tyr Pro Asp Ala Lys Lys Val Leu
    210                 215                 220

Glu Glu Arg Gly Arg Glu Ile Leu Met Lys Met Gly Leu Leu Asp
225                 230                 235
```

EXPRESSION OF FUNCTIONAL HUMAN OLFACTORY CYCLIC NUCLEOTIDE GATED (CNG) CHANNEL IN RECOMBINANT HOST CELLS AND USE THEREOF IN CELL BASED ASSAYS TO IDENTIFY SMELL MODULATORS

RELATED APPLICATIONS

This application claims benefit of priority to U.S. provisional patent application Ser. No. 60/303,140 filed on Jul. 6, 2001 and U.S. provisional patent application Ser. No. 60/337,154 filed on Dec. 10, 2001, both of which are incorporated by reference in their entirety herein.

FIELD OF THE INVENTION

The present invention relates to isolated nucleic acid sequences that encode human olfactory cyclic nucleotide gated (CNG) channel subunits, and the corresponding polypeptides. The invention further relates to the use of human CNG channels to profile, screen for, and identify compounds that modulate the human olfactory CNG channel. More specifically, the invention relates to the expression of the human olfactory CNG channel in cells, preferably mammalian or insect cells, and the use of these cells in high throughput cell-based assays to identify compounds that enhance or block human olfactory CNG function. Compounds that activate the olfactory CNG channel will enhance smell and can be used to make foods more palatable for individuals with attenuated olfactory function. Conversely, compounds that inhibit the olfactory CNG channel will inhibit smell and can be use to block malodors. Additionally, the invention relates to the use of cell-based olfactory CNG channel assays to identify modulators of G-protein coupled receptor (GPCRs) and other proteins that regulate cyclic nucleotide levels.

BACKGROUND OF THE INVENTION

The interaction of odorants with olfactory receptors on the apical cilia of olfactory neurons is the first step in our perception of smell. The large number (e.g., approximately 400 in humans) and structural diversity of the opsin-like GPCRs that function as olfactory receptors underlies our ability to detect and discriminate a vast number of volatile compounds (Buck and Axel, 1991, Fuchs et al., 2001). Although there appear to be several hundred different olfactory neuron cell types in humans—each expressing a different olfactory receptor gene (Chess et al., 1994; Malnic et al., 1999; Touhara et al., 1999)—several lines of evidence argue that signal transduction in olfactory neurons involves a common downstream signaling pathway that involves the second messenger cAMP. Many odorants have been shown to elicit an increase in cAMP in olfactory neurons (Breer, 1993). Moreover, mouse knockout studies with the $G_s$-like G protein $G_{olf}$ (Jones and Reed, 1989; Belluscio et al., 1998), type III adenylyl cyclase (Bakalyar and Reed, 1990; Wong et al., 2000), and an olfactory CNG channel subunit (Dhallan et al., 1990; Brunet et al., 1996) have demonstrated that these signaling molecules play an obligate role in olfactory signal transduction. In summary, olfactory signal transduction is believed to involve the following steps: (1) an olfactory stimulus activates an olfactory receptor; (2) the activated olfactory receptor activates $G_{olf}$; (3) type III adenylyl cyclase is activated by $G_{olf}$ and catalyzes cAMP synthesis; (4) the olfactory CNG channel is activated by cAMP; (4) ion flux through the activated olfactory CNG channel depolarizes the olfactory neuron and initiates the generation of action potentials (Gold, 1999).

CNG channels are composed of structurally related subunits with six transmembrane segments and C-terminal nucleotide-binding domains (Zagotta and Siegelbaum, 1996). The first subunit, OCNC1, of the olfactory neuron-specific CNG channel to be identified was cloned from rat olfactory cDNA based on its homology to retinal CNG channel subunits (Dhallan et al., 1990). Discrepancies between the native olfactory CNG channel conductance and sensitivity to cAMP and cGMP and the properties of heterologously expressed OCNC1 channels motivated the search for additional CNG channel subunits. Two additional subunits, OCNC2, and β1 b (a splice variant of a rod photoreceptor CNG channel subunit), were subsequently identified by homology-based cloning from rodent olfactory cDNA (Liman and Buck, 1994; Bradley et al., 1994; Sautter et al., 1998; Bonigk et al., 1999). Histochemical experiments demonstrated that these molecules are selectively expressed in the apical cilia of olfactory neurons. And heterologous coexpression of the olfactory CNG subunits produced channels with native-like properties (Sautter et al., 1998; Bonigk et al., 1999). Therefore, the olfactory CNG channel may be composed of three different subunits. (OCNC1 is also called CNG2, CNGC4, CNCα3, and olfactory CNG channel α; OCNC2 is also called CNG5, CNCα4, and olfactory CNG channel β; β1b is also called CNCβ1b and CNG4.3.)

Olfactory CNG channels are compelling targets for smell modulators. First, the channels are localized to the apical cilia of olfactory neurons and exposed on the external surface of the olfactory epithelium. Therefore, channel activators do not have to cross cell membranes. Second, olfactory CNG channels can be functionally expressed in heterologous cells (Sautter et al., 1998; Bonigk et al., 1999; Qu et al., 2000). Third, calcium-imaging-based assays, which are amenable to high-throughput screening with automated fluorometric instrumentation, can be used to measure CNG channel activity because these channels are permeable to $Ca^{2+}$. Indeed, calcium imaging has been used to record odorant-dependent activation of olfactory neurons in primary culture (Hirono et al., 1992; Ma and Shepherd, 2000), and a calcium-dye-based assay was recently developed for rat OCNC1 expressed in heterologous cells (Rich et al., 2001). Fourth, these channels are gated by cyclic nucleotides—i.e., they are allosterically activated by small molecules. Finally, several small molecules have been identified that may modulate smell by directly inhibiting CNG channel activity (Kurahashi et al., 1994). And there is ample precedent for small-molecules that activate non-ionotropic receptor ion channels such as dihydropyridine agonists of L-type $Ca^{2+}$ channels (Hockerman et al., 1997).

Rodent olfactory CNG channels have been expressed in *Xenopus* oocytes and HEK-293 cells, and they have been functionally characterized by direct measurement of the electrical properties of CNG channel-containing membranes (Sautter et al., 1998; Bonigk et al., 1999; Qu et al., 2000). However, electrophysiological assays are not amenable to high-throughput screening. To overcome this limitation, the present invention describes a cell-based fluorometric assay that is amenable to automated high-throughput screening for olfactory CNG channel modulators. This assay uses fluorescent calcium or membrane potential dyes to quantitate ion flux through olfactory CNG channels expressed in HEK-293 cells following elevation of cAMP levels caused by the adenylyl cyclase activator forskolin. In addition, the invention identifies nucleic acid sequences that encode human olfactory CNG channel subunits, which had not been identified prior to this invention.

SUMMARY OF THE INVENTION

The present invention encompasses isolated OCNC1, OCNC2 and β1b subunit polypeptides of the human olfactory CNG channel, and the nucleic acid sequences that encode them. The invention also includes means for expressing such nucleic acid sequences, including vectors containing such nucleic acid sequences, and host cells containing such vectors. The invention further encompasses methods for using such nucleic acids, vectors, and host cells to identify compounds that modulate smell by modulating olfactory CNG channel activity. Also, the assays described in the invention could be adapted to quantitate the activity of GPCRs and other proteins that regulate cyclic-nucleotide levels.

In a preferred embodiment, host cells that express the human olfactory CNG channel are first stimulated with an agent that increases cAMP such as the adenylyl cyclase activator forskolin, the phosphodiesterase inhibitor IBMX, or membrane-permeant cyclic-nucleotide analogs. Olfactory CNG channel activation is then quantitated by monitoring ion flux into treated cells using fluorescent calcium chelators such as fura-2 (Abe et al., 1992); fluorescent sodium chelators such as sodium green tetraacetate (Molecular Probes) and the $Na^+$-Sensitive Dye Kit (Molecular Devices); or membrane potential dyes such as the Membrane Potential Dye Kit (Molecular Devices) and the Oxanol-Coumarin Kit (Aurora Biosciences). Smell-enhancing olfactory CNG channel activators could then be identified by their ability to potentiate the fluorescent response to increased cAMP, and smell-blocking channel antagonists could be identified by their ability to attenuate the fluorescent response. Such assays are amenable to high-throughput screening of compound libraries using automated fluorometric instrumentation such as the Fluorometric Imaging Plate Reader (FLIPR, Molecular Devices) and the Voltage Ion Probe Reader (VIPR, Aurora Biosciences).

OBJECTS AND PREFERRED EMBODIMENTS OF THE INVENTION

It is an object of the invention to provide isolated nucleic acid sequences that encode the OCNC1, OCNC2 and β1b subunits of human olfactory CNG channel, variants and functional fragments, mutants, and chimeras thereof; including e.g., splice variants, allelic variants, single nucleotide polymorphisms (SNPS) and mutational variants produced by recombinant or chemical means.

It is another object of the invention to provide isolated OCNC1, OCNC2 and/or β1b subunit polypeptides of the human olfactory CNG channel and functional fragments, chimeras and variants thereof, including splice variants, allelic variants, SNPS mutants produced by chemical or recombinant methods and non-human primate orthologs thereof.

It is another object of the invention to produce a cell line that expresses a functional human CNG channel polypeptide subunit or combination of subunits.

It is a preferred object of the invention to produce a cell line that functionally expresses each of human OCNC1, OCNC2 and β1b subunit polypeptides (preferably having the amino acid sequences contained in SEQ ID NO.: 1, 2 and 3 respectively) or a functional, chimera, or mutant encoded by the DNA sequences or fragment of each of said subunit polypeptides.

It is a more preferred object of the invention to provide a mammalian cell line, such as a human embryonic kidney cells (HEK293 cells), COS cells, mouse L cells, chimeric hamster, ovary cells, Africa green monkey kidney cells, LtK-cells and BHK cells that expresses a functional human olfactory CNG channel.

It is another preferred object of the invention to use such cell lines to identify compounds that modulate smell by modulating olfactory CNG channel activity.

It is also an object of the invention is to use such cell lines to quantitate the activity of GPCRs and other proteins that regulate cyclic-nucleotide levels.

It is a more specific object of the invention to use cell lines that stably or transiently express a functional human CNG channel in assays wherein the CNG channel is initially stimulated with an agent that increases cAMP such as an adenylyl cyclase activator, e.g., forskolin, or a phosphodiesterase inhibitor, e.g., IBMX, or a membrane-permeant cyclic-nucleotide analogs and CNG channel activation is then quantitated by measuring ion flux into cells, e.g., by use of fluorescent calcium chelators, or fluorescent sodium chelators.

It is another specific object of the invention to use cell lines that stably or transiently express a functional human CNG channel for high throughput screening of compound libraries using automated fluorometric instrumentation such as the Fluorometric Imaging Plate Reader (FLIPR, Molecular Devices) and the Voltage Ion Probe Reader (VIPR, Aurora Biosciences).

Specifically, it is an object of the invention to identify compounds that modulate odor perception by assaying the effects of compounds on HEK-293 cell lines that express a functional human olfactory CNG channel using a calcium imaging assay.

It is another specific object of the invention to provide high-throughput CNG plate-based assays wherein a human CNG channel is activated using cell-permeant cAMP or cGMP (delivered via flash photolysis) and the activated CNG channel is used to identify compounds that modulate odor perception.

It is a more specific object of the invention to produce HEK-293, insect cells or *Xenopus* oocytes that express a functional human olfactory CNG channel.

It is another specific object of the invention to produce HEK-293 or insect cells or *Xenopus* oocytes that express a human ortholog of at least one of rat OCNC1, rat OCNC2 and rat β1b genes, and preferably all three.

It is another specific object of the invention to produce HEK293 or insect cells or *Xenopus* oocytes that express a variant of β1b protein with enhanced sensitivity to cAMP and cGMP.

It is a another specific object of the invention to provide a plate-based assay for selecting compounds that modulate odor perception comprising:
 (i) providing mammalian or insect cells that express a functional human CNG channel;
 (ii) stimulating said cells to increase intracellular cAMP/cGMP levels thereby activating the CNG channel;
 (iii) comparing cation flux in the presence or absence of a compound for its modulatory effect on CNG activity; and
 (iv) testing the effect of modulating compounds on odor perception.

BRIEF DESCRIPTION OF THE FIGURES

FIG. 1. The human genome contains orthologs of the three rat olfactory CNG channel subunits. Pairwise sequence identities for paralogs range from 30-50%, orthologs 84-90%. Sequences corresponding to the C-terminal cyclic-nucleotide-binding domains of the rat and human CNG channel subunits are shown. Sequences for the human OCNC1, OCNC2, and β1b olfactory CNG channel subunits of this invention are SEQ ID NOs: 1-3, respectively; database sequences for the rat CNG channel subunits OCNC1, OCNC2 and β1b are accessions NM_012928, NM_053496, and AJ000515, respectively (SEQ ID NOs: 5-7, respectively).

FIG. 2. Sequence of hOCNC1 (SEQ ID NO: 1). This cDNA sequence corresponds to the hOCNC1 allele contained in the cloned genomic interval HSAF002992.

FIG. 3. Sequence of hOCNC2 (SEQ ID NO: 2). This cDNA sequence corresponds to the hOCNC2 allele contained in the cloned genomic interval AC022762.

FIG. 4. Sequence of hβ1b (SEQ ID NO: 3). This cDNA sequence represents a novel allele.

DETAILED DESCRIPTION OF THE INVENTION

Figure 5:
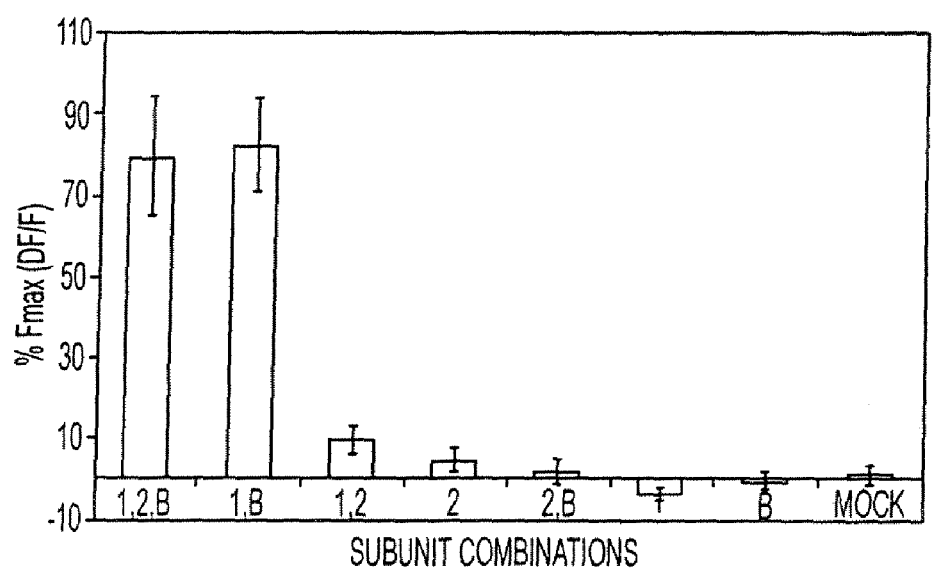
FIG. 5. Olfactory CNG channel activity is dependent on subunit composition. Fluorescence increases at 6 minutes following 50 μM forskolin addition were determined for cells transfected with different combinations of human olfactory CNG channel subunits and loaded with a calcium dye. Activities represent the mean±s.e. of 8 independent responses and were normalized to fluorescence increases at 6 minutes following addition of the calcium ionophore ionomycin. OCNC1 is abbreviated as '1', OCNC2 as '2', and β1b as 'B'.

Prior to discussing the invention in further detail the following definitions are provided. In all other instances words and phrases are to be accorded their ordinary meaning as they would be construed by one skilled in the relevant art.

DEFINITIONS

"Functional Human Olfactory CNG Channel" refers to an olfactory neuron-specific CNG unit comprised of at least one human olfactory CNG channel subunit, variant or fragment thereof. Such CNG subunits include OCNC1, OCNC2 and β1b. A functional channel will be sufficiently permeable to extracellular cations to produce detectable changes in intracellular cations using either a membrane potential-sensitive fluorescent dye or a calcium-sensitive fluorescent dye.

Figure 1:
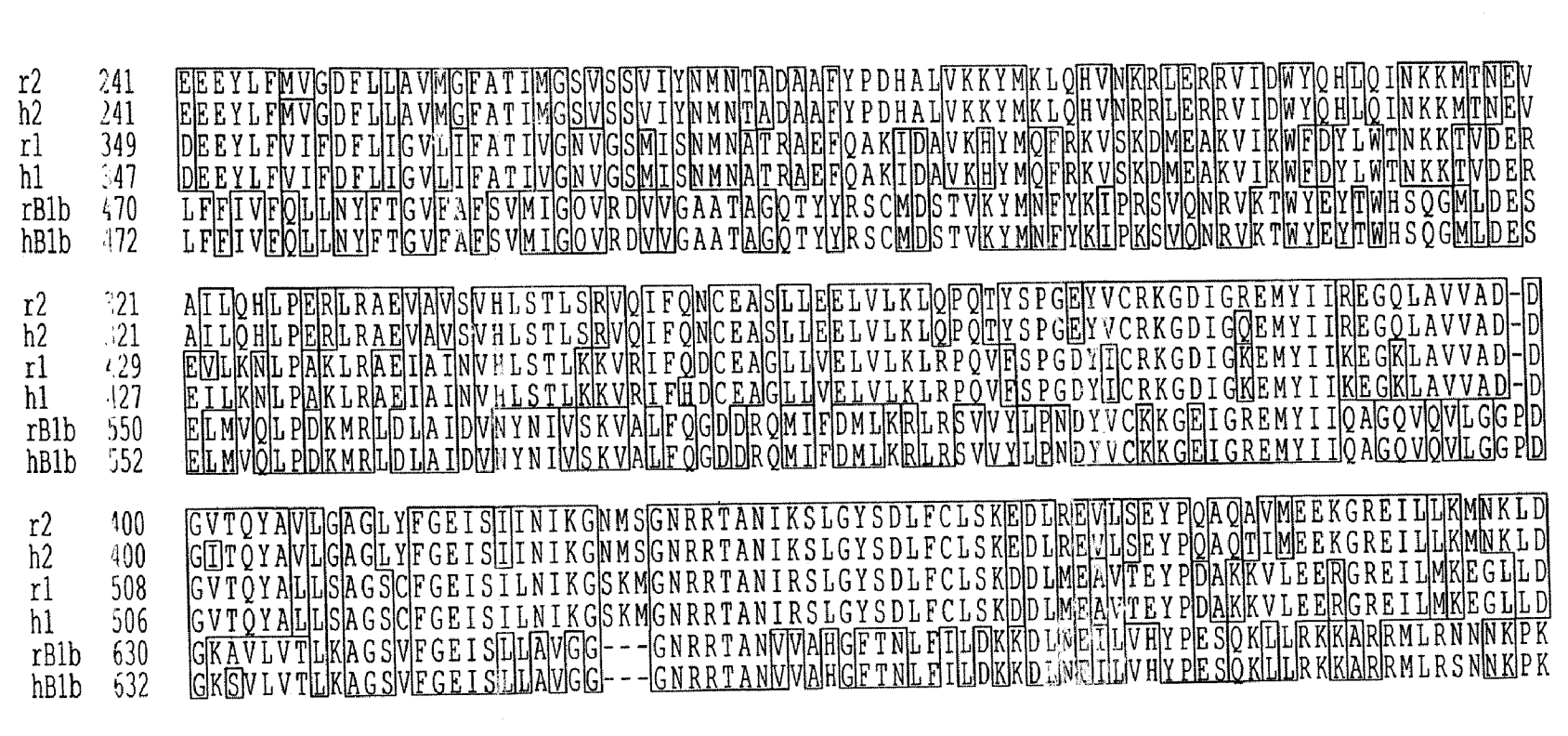

"Human Olfactory CNG Channel Subunit" refers to a human ortholog of a rat olfactory polypeptide selected from rat OCNC1, rat OCNC2 and rat β1b, or a DNA that exhibits at least 60%, preferably at least 70%, more preferably at least 80-90%, and still more preferably at least 90-99% sequence identity with wild-type human OCN1, human OCN2 and human β1b. In a preferred embodiment, the human ortholog will comprise a sequence as shown in FIG. 1, or a fragment or variant thereof that exhibits at least 80%, more preferably at least 90%, and still more preferably at least 95-99% identical thereto. Further variants or fragments can be selected based on their ability upon expression alone or in combination with other CNG subunits to produce functional olfactory (calcium permeable) CNG subunits.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated," when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

The terms "amplifying" and "amplification" refer to the use of any suitable amplification methodology for generating or detecting recombinant or naturally expressed nucleic acid, as described in detail, below. For example, the invention provides methods and reagents (e.g., degenerate oligonucleotide primer pairs) for amplifying (e.g., by polymerase chain reaction, PCR) naturally expressed (e.g., genomic or mRNA) or recombinant (e.g., cDNA) nucleic acids of the invention (e.g., sensant-binding sequences of the invention) in vivo or in vitro.

The term "expression vector" refers to a vehicle used in any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

The term "library" means a preparation that is a mixture of different nucleic acid or polypeptide molecules, such as the library of recombinantly generated sensory, particularly olfactory or taste, receptor ligand-binding domains generated by amplification of nucleic acid with degenerate primer pairs, or an isolated collection of vectors that incorporate the amplified sensant-binding domains, or a mixture of cells each randomly transfected with at least one vector encoding a sensory receptor.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones, see e.g., *Oligonucleotides and Analogues, a Practical Approach*, ed. F. Eckstein, Oxford Univ. Press (1991); *Anti-sense Strategies*, Annals of the N.Y. Academy of Sciences, Vol. 600, Eds. Baserga et al. (NYAS 1992); Milligan (1993) *J. Med. Chem.* 36:1923-1937; *Antisense Research and Applications* (1993, CRC Press), WO 97/03211; WO 96/39154; Mata (1997) *Toxicol. Appl. Pharmacol.* 144:189-197; Strauss-Soukup (1997) *Biochemistry* 36:8692-8698; Samstag (1996) *Antisense Nucleic Acid Drug Dev* 6:153-156.

The terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art.

For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or val; Lys/Arg or Gin or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, *Proteins*, W.H. Freeman, 1984; Schultz & Schimer, *Principles of Protein Structure*, Springer-Verlag, 1979). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains or sensant-binding domains or chimeric receptors of the invention. The mimetic can be either entirely composed of synthetic, non-natural analogs of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond")

linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$), thiazole, retroamide, thioamide, or ester (see, e.g., Spatola (1983) in *Chemistry and Biochemistry of Amino Acids, Peptides and Proteins, Vol.* 7, pp 267-357, "Peptide Backbone Modifications," Marcell Dekker, NY). A polypeptide can also be characterized as a mimetic by containing all or some non-natural residues in place of naturally occurring amino acid residues; non-natural residues are well described in the scientific and patent literature.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The term "transmembrane domain" means a polypeptide domain that can completely span the plasma membrane. The general secondary and tertiary structure of transmembrane domains, in particular the seven transmembrane domains of 7-transmembrane receptors such as olfactory receptors, are well known in the art. Thus, primary structure sequence can be designed or predicted based on known transmembrane domain sequences, as described in detail below.

The terms "CNG channel" subunit protein or a fragment thereof, or a nucleic acid encoding one of three subunits of "CNG channel" protein or a fragment thereof refer to nucleic acids and polypeptides, polymorphic variants, alleles, mutants, and interspecies homologues that: (1) have an amino acid sequence that has greater than about 80% amino acid sequence identity, 85%, 90%, preferably 91%, 92%, 93%, 94%, 95%, 96%, 97%, 98% or 99% or greater amino acid sequence identity, preferably over a region of at least about 25, 50, 100, 200, or 500, or more amino acids, to an amino acid sequence encoded by the cDNA contained in SEQ ID NO:1; 2 or 3; or (2) specifically bind to antibodies, e.g., polyclonal antibodies, raised against an immunogen comprising an amino acid sequence encoded by SEQ ID NO:1, 2, or 3 or immunogenic fragments thereof, and conservatively modified variants thereof; or (3) specifically hybridize under stringent hybridization conditions to an anti-sense strand corresponding to a nucleic acid sequence encoding a human CNG protein, e.g., SEQ ID NO:1, 2, or 3 or their complements, and conservatively modified variants thereof; or (4) have a nucleic acid sequence that has greater than about 80% sequence identity, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to SEQ ID NO:1, 2, or 3 or their complements, or (5) is functionally equivalent to the human CNG described herein, e.g., as determined by measurable in fluorescence of a membrane potential dye in response to cations.

Functionally equivalent CNG channel proteins include subunits with primary sequences different than those identified infra, but which possess an equivalent function as determined by functional assays. By "determining the functional effect" refers to assaying the effect of a compound that increases or decreases a parameter that is indirectly or directly under the influence of an CNG channel polypeptide e.g., functional, physical and chemical effects. Such functional effects include, but are not limited to, changes in ion flux, membrane potential, current amplitude, and voltage gating, a as well as other biological effects such as changes in gene expression of any marker genes, and the like. The ion flux can include any ion that passes through the channel, e.g., sodium or lithium and analogs thereof such as radioisotopes. Such functional effects can be measured by any means known to those skilled in the art, e.g., by the use of two electrode electrophysiology or voltage-sensitive dyes, or by measuring changes in parameters such as spectroscopic characteristics (e.g., fluorescence, absorbance, refractive index), hydrodynamic (e.g., shape), chromatographic, or solubility properties.

"Inhibitors", "activators", and "modulators" of CNG channel polynucleotide and polypeptide sequences are used to refer to activating, inhibitory, or modulating molecules identified using cell-based assays of CNG channel polynucleotide and polypeptide sequences. Inhibitors are compounds that, e.g., bind to, partially or totally block activity, decrease, prevent, delay activation, inactivate, desensitize, or down regulate the activity or expression of CNG channel proteins, e.g., antagonists. "Activators" are compounds that increase, open, activate, facilitate, enhance activation, sensitize, agonize, or up regulate CNG channel protein activity. Inhibitors, activators, or modulators also include genetically modified versions of CNG channel proteins, e.g., versions with altered activity, as well as naturally occurring and synthetic ligands, antagonists, agonists, peptides, cyclic peptides, nucleic acids, antibodies, antisense molecules, ribozymes, small organic molecules and the like. Such assays for inhibitors and activators include, e.g., expressing CNG channel protein in cells, cell extracts, or cell membranes, applying putative modulator compounds, and then determining the functional effects on activity, as described above.

Samples or assays comprising CNG channel proteins that are treated with a potential activator, inhibitor, or modulator are compared to control samples without the inhibitor, activator, or modulator to examine the extent of activation, inhibition or modulation.

The term "test compound" or "test candidate" or "modulator" or grammatical equivalents thereof as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid (e.g., a sphingolipid), fatty acid, polynucleotide, oligonucleotide, etc., to be tested for the capacity to modulate CNG channel activity. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., enhancing activity, creating variants of the lead compound, and evaluating the property and activity of those variant compounds. Preferably, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" includes sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 80% identity, preferably 85%, 90%, 91%, 92%, 93%, 94%, 95%, 96%, 97%, 98%, 99%, or higher identity over a specified region (e.g., nucleotide sequences SEQ ID NO: 1, 2, or 3), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein and refer to a polymer of amino acid residues. The terms apply to amino acid polymers in which one or more amino acid residue(s) is (are) an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but those functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologous, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)). As noted previously, the invention embraces cells that express ENaC subunit polypeptides having primary sequences different than those disclosed in the subject application that are functionally equivalent in appropriate assays, e.g., using whole cell sodium conductance assays described in detail infra.

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered three-dimensional structures within a polypeptide. These structures are commonly known as domains, e.g., transmembrane domains pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of; β-sheet and α-helices. "Tertiary structure" refers to the complete three-dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

CNG channel nucleic acid sequences also include single nucleotide polymorphisms which encode CNG channel subunits that are functionally equivalent to the human CNG channel polypeptides disclosed herein when assayed using appropriate assays, e.g., the fluorescence assays described herein.

Membrane potential dyes or voltage-sensitive dyes refer to a molecule or combinations of molecules that change fluorescent properties upon membrane depolarization.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. In the present invention this typically refers to cells that have been transfected with nucleic acid sequences that encode one or more human CNG channel subunits.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein). The term "heterologous" when used with reference to cellular expression of a gene, cDNA, mRNA or protein indcates that the gene, cDNA, mRNA, or protein is not normally expressed in the cell or is from another species than the original source of the cells.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mug alpha, delta, or epsilon, which in turn define the immunoglobulin classes, IgG, IgM, IgA, IgD and IgE, respectively. Typically, the antigen-binding region of an antibody will be most critical in specificity and affinity of binding.

Particularly, such an antibody includes one which specifically binds to a human CNG channel subunit polypeptide disclosed herein, or a mixture of antibodies that specifically bind such CNG channel subunit polypeptides.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to CNG channel subunit proteins or polymorphic variants, alleles, orthologs, and conservatively modified variants, or splice variants, or portions thereof, can be selected to obtain only those polyclonal antibodies that are specifically immunoreactive with CNG channel subunit proteins i.e., OCNC1, OCNC2 and β1b those having the amino acid sequences encoded by the cDNAs contained in SEQ ID NO.: 1, 2, and 3, and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that cars be used to determine specific immunoreactivity).

Thus, the present invention encompasses isolated nucleotide sequences encoding a human OCNC1 olfactory CNG channel submit, wherein said nucleotide sequence has at least about 95% identity to SEQ ID NO: 1; isolated nucleotide sequences encoding a human OCNC2 olfactory CNG channel subunit, wherein said nucleotide sequence has at least about 95% idenity to SEQ ID NO: 2; and isolated nucleotide sequences encoding a human β1b olfactory CNG channel subunit, wherein said nucleotide sequence has at least about 95% identity to SEQ ID NO: 3.

More preferably, the invention encompasses isolated nucleotide sequences that hybridize under high stringency conditions to SEQ ID NO: 1-3. The term "nucleotide sequences" is intended to encompass both RNA and DNA, having any number of strands, e.g., single-stranded and double-stranded. Use of the terms "isolated" or "purified" in the present specification and claims as a modifier of DNA, RNA, pol peptides, or proteins means that the DNA, RNA, polypeptides, or proteins so designated have been separated from their native cellular environment, and may be produced in such form at will by the hand of man, i.e., recombinantly. High stringency conditions are: hybridization in 6×SSC, 5× Denhart's solution, 0.3% SDS, 2 mM EDTA, and 1 mM sodium pyrophosphate at 65° C. followed by washing in 0.1×SSC and 0.1% SDS at 65° C.

Polypeptides

The present invention also includes isolated polypeptides encoded by the nucleotide sequences of the invention, which includes human olfactory CNG channel subunit polypeptides, both individually and in complexes with each other and other proteins. It should be clear to those of skill in the art that the same polypeptide could be encoded by different nucleotide sequences given the degeneracy of the triplet coding scheme. Accordingly, degenerate nucleic acids encoding the same proteins as disclosed herein would also be encompassed in the scope of the invention.

Polynucleotide and Protein Variants

The present invention also encompasses variants and mutants of the nucleotide and protein subunit sequences disclosed herein, particularly sequences including mutations that alter the activity of CNG channels formed from such subunits. A particularly preferred mutant of OCNC1 is represented by SEQ ID NO: 4, wherein said sequence differs from SEQ ID NO: 1 as it has the mutations C458W and E581M.

Expression Sequences

The invention also includes isolated expression sequences containing the nucleotide sequences disclosed herein, wherein coding sequences for CNG channel subunits are operably linked to transcriptional and translational regulatory sequences. Such expression sequences could include the native coding sequence in combination with the native promoter region. Alternatively, expression constructs could be constructed whereby the coding sequence is operably linked to a heterologous promoter region, e.g., for expression in a particular host cell. Also envisioned are recombinant reporter constructs, wherein the coding sequences are fused in part or in total to a reporter sequence encoding a selectable or screenable marker. An "expression sequence" or construct could be transfected into a host cell in the absence of a vector, and be incorporated into the chromosome of the host cell.

Expression Vectors

The present invention also includes expression vectors containing the sequences disclosed herein, and host cells containing such vectors. An "expression vector" means that the vector expresses the sequence of the gene that it contains. However, also included in the invention are other vectors (and host cells) containing the nucleotide sequences disclosed herein, wherein such other vectors are not necessarily "expression" vectors, but rather are vectors containing the coding sequence but not expressing the polypeptide, for example as a means of propagating the vector or sequencing the gene.

Host Cells

Also included in the invention are host cells containing at least one of the expression constructs or vectors of the present invention in addition to an expression construct or vector expressing another CNG channel subunit, wherein the expressed polypeptides associate and form a partial or total functional CNG channel on the surface of said cells. Suitable host cells for use in the present invention include human embryonic kidney cells (preferably HEK-293), COS cells, mouse L cells, Chinese hamster ovary cells, African green monkey kidney cells, Ltk-cells, and BHK cells. It should be clear to those of skill in the art that sequences necessary for expression in a particular host cell, i.e., promoters, upstream untranslated regions, transcriptional termination sequences, vector propagation sequences, etc. may vary depending on the host cell employed, and could be readily chosen from the molecular tools known and available in the art.

Olfactory CNG Channel Assays

The present invention also encompasses assays employing the nucleic acids, proteins, vectors and host cells disclosed herein. Such assays include those designed to measure changes in CNG channel activity or in the activity of proteins or second messengers associated with CNG channel activity, i.e., for the purpose of identifying ligands or screening small molecules to be used in blocking or enhancing olfactory signaling. For instance, the invention includes cation-based assays for monitoring changes in CNG channel activation comprising (1) introducing one or more nucleic acids encoding and expressing at least one human olfactory CNG channel subunit into host cells wherein said at least one CNG channel subunit forms a functional CNG channel; and (2) measuring changes in the amount of activation of said CNG channel in the presence and absence of different stimuli wherein said changes are measured via a change in the level of one or more intracellular cations. As described herein, functional CNG channels may be formed by the expression of all three subunits, or by expressing just ONCN1 and ONCN2, or by expressing ONCN1 alone. In this sense, "functional" means forming a channel through which extracellular cations may enter and changes in the level of intracellular cations due to CNG stimulation or inhibition may be measured and quantitated.

In such assays, at least one functional human olfactory CNG channel subunit is preferably encoded by a sequence selected from the group consisting of sequences that hybridize under high stringency conditions to SEQ ID NO: 1. This subunit can be expressed alone or in combination with other olfactory CNG channel subunits to form a functional CNG channel; i.e., a cation channel regulated by cyclic-nucleotides. For instance, the OCNC1 subunit may be expressed along with OCNC2 and/or β1b subunits, particularly those encoded by the nucleic acids of the invention that hybridize wider high stringency conditions to SEQ ID Nos.: 2 and 3, respectively. Orthologs of CNG channel subunits, i.e., OCNC2 and/or β1b subunits from other species, may also be expressed in the assays of the invention along with human CNG channel subunits, for instance, a human OCNC1 subunit, where the coexpression of such subunits forms a functional chimeric CNG channel.

Such assays of the invention could be used to identify modulators of olfactory CNG channels that modulate smell. In such assays, the host cells may be first stimulated with an agent that induces a basal level of CNG activation such as forskolin (or other activators of adenylyl cyclase), IBMX (or other inhibitors of cAMP phosphodiesterase), or membrane-permeant analogs of cAMP or cGMP. Reagents that directly activate the olfactory CNG channel—such as compounds that generate nitric oxide, which activates the channel by S-nitrosylation (Broillet, 2000)—can also be used. Olfactory CNG channel activation is then quantitated by monitoring ion flux into treated cells using fluorescent calcium chelators such as fura-2 (Abe et al., 1992); fluorescent sodium chelators such as sodium green tetraacetate (Molecular Probes) and Na$^+$-Sensitive Dye Kit (Molecular Devices); or membrane potential dyes such as the Membrane Potential Dye Kit (Molecular Devices) and the Oxanol-Coumarin Kit (Aurora Biosciences). Smell-enhancing olfactory CNG channel activators could then be identified by their ability to potentiate the fluorescent response to increased cAMP, and smell-blocking channel antagonists could be identified by their ability to attenuate the fluorescent response. The olfactory CNG channel could also be used as a surrogate for the identification of modulators of other CNG channels.

Assays for GPCRs and Other Proteins that Regulate cAMP Levels

The present invention also encompasses assays for proteins that regulate cyclic-nucleotide levels. Such assays include those designed to measure changes in CNG channel activity resulting from changes in cyclic-nucleotide levels. Preferably, sensitized olfactory CNG channels that make use of subunit variants such as OCNC1 [C458W/E581M] (SEQ ID NO: 4) can be used to increase the sensitivity of these assays. Such assays can be used to quantitate the activity of GPCRs that couple to G proteins that regulate adenylyl cyclases or phosphodiesterases, and to identify GPCR modulators by high-throughput screening.

For instance, a nucleic acid encoding a G-protein coupled receptor may also be introduced into the host cells used in the assays of the invention, in addition to nucleic acids encoding one or more CNG channel subunits and nucleic acids encoding G proteins if necessary. Suitable G-protein coupled receptors include odorant receptors, taste receptors, vomeronasal organ (VNO) receptors, mu opiate receptors, muscarinic acetylcholine receptors, adrenergic receptors, serotonin receptors, dopamine receptors, angiotensin receptors, adenosine receptors, bradykinin receptors, metabotropic excitatory amino acid receptors, to name a few. In such an assay, stimuli could be screened for potential modulators of G-protein coupled receptor activity, via an affect of subsequent cyclic nucleotide levels on CNG channel activity.

When a G protein coupled receptor is also expressed in the cells of the assays of the invention, preferably the G-protein coupled receptor is an olfactory receptor. Such cells may be screened for stimuli that result in activation of the G protein receptor, i.e. odorant ligands that interact with the odorant receptor, thereby leading to CNG activation. Also contemplated are assays in which the G-protein coupled receptor is first activated by exposure to a ligand, and said cells are screened for stimuli that increase the activation of said receptor, thereby leading to an increase in CNG activation (i.e., odorant enhancers). Such enhancers could act at the level of the receptor or the CNG channel to increase CNG channel activation. Such enhancers could also act on adenylyl or guanylyl cyclase, phosphodiesterase, or any other protein that regulates cyclic nucleotide levels. Alternatively, such cells could be screened for stimuli that decrease the activation of the receptor, or the activation of CNG channel activity via the receptor, thereby leading to a decrease in CNG activation (i.e. odorant blockers).

The invention also encompasses variations of any assay described herein further comprising the use of control cells. For instance, assays including expression of a desired G protein-coupled receptor could further comprise the steps of: (a) providing a second host cell that expresses said at least one CNG channel subunit so as to form a functional CNG channel but that does not express said G-protein coupled receptor; (b) measuring changes in the amount of activation of the CNG channel in said second host cell in the presence and absence of different stimuli; and (c) comparing said changes in the amount of activation of said CNG channel in said second host with the amount of activation of said CNG channel in said cell expressing said G-protein coupled receptor.

Assays for Identifying Nucleic Acids Encoding Proteins Involved in Sensory Signaling As described in greater detail infra, the present invention also encompasses methods for identifying nucleic acids encoding proteins involved in sensory responses, particularly proteins that act in concert with CNG channels. For instance, a nucleic acid encoding a G protein-coupled receptor from a cell responding to a particular sensory signal could be identified by (1) introducing one or more nucleic acids encoding and expressing at least one human olfactory CNG channel subunit into host cells wherein said at least one CNG channel subunit forms a functional CNG channel; (2) introducing a library of cDNAs or RNAs isolated from a sensory cell of interest into said mammalian or *Xenopus* host cell; and (3) exposing the transfected host cells to the known sensory ligand to identify a transfected host cell that expresses a G protein-coupled receptor that binds to the ligand.

High-Throughput Assays

The assays of the present invention particularly include high-throughput screening assays. Apparatuses for quantitating simultaneously measurements from a multitude of samples are known in the art. For example, a Fluorometric Imaging Plate Reader (FLIPR) is available from Molecular Devices, and may be used for single wavelength detection of changes in intracellular calcium or sodium, membrane potential and pH. The apparatus and reader can be programmed to simultaneously deliver compounds to and image all 96 wells of a microplate within one second, and is therefore amendable to high throughput formats. An argon-ion laser excites a fluorescent indicator dye suitable for the specific change being measured, and the emitted light is detected using the associated optical system. A camera system then images the entire plate and integrates data over a time interval specified by the user.

Alternatively, apparatuses such as the Voltage Ion Probe Reader (VIPR) of Aurora Biosciences may be used for dual wavelength detection of fluorescence resonance energy transfer (FRET) between two fluorescent molecules. FRET is a distance-dependent interaction between the electronic excited states of two dye molecules, and may be used to investigate a variety of biological events that produce changes in molecular proximity, including the activity of Na+, K+, Cl−, Ca2+, and Ligand-gated Ion Channels. Aurora Biosciences Corporation's voltage sensor probe technology uses FRET between a membrane-bound donor molecule and a mobile, voltage-sensitive, acceptor molecule to detect membrane potential. The VIPR reader is amenable to both 96- and 384-well formats.

The high-throughput assays of the invention include a variety of formats. For instance, one embodied high throughput assay for detecting or measuring the activity of a CNG channel in response to at least two or more potential test compounds in at least two or more individual compartments simultaneously, comprises (1) introducing one or more nucleic acids encoding and expressing at least one olfactory CNG channel subunit into suitable host cells wherein said at least one CNG channel subunit forms a functional CNG channel such that, when activated either directly or indirectly, said channel causes a change in the intracellular concentration of a predetermined ion; (2) transferring said host cells to a divided culture vessel having an array of individual compartments (either before or after transfection); (3) loading said host cells with an ion-sensitive fluorescent indicator sufficient to detect a change in the concentration of a predetermined ion; (4) delivering to said at least two or more individual compartments one or more different test compounds or combination of test compounds wherein said test compounds have the potential either directly or indirectly to activate said CNG channel; and (5) detecting or measuring in at least two of said compartments the fluorescence emitted by the ion-sensitive indicator in order to detect a change in the concentration of the predetermined ion in response to potential activation of said CNG channel. While the assay may be used to simultaneously measure at least two samples as mentioned above, preferred high throughput formats preferably involve the screening of at least 5, more preferably 10, more preferably 50, more preferably 100, and possibly even hundreds or thousands of samples simultaneously. The number of samples screened in a single throughput may be based on the number of individual compartments in the particular plate to be used, i.e., 24, 96, 384, etc.

In a variation of the high throughput assays of the invention, at least one of the individual compartments in the array may be exposed to a known activator of CNG channels at the same time that said at least two compartments are exposed to said test compounds. Such a further compartment would serve as a positive control for the detection of CNG channel activity. Compartments containing suitable negative controls could also be included. Known activators of CNG channels that may be used for positive controls include forskolin, IBMX, permeant analogs of cAMP and cGMP, and nitric oxide (NO)-generating compounds (such as S-nitrosocysteine—SNC).

Any cell amenable to a high throughput format may used in the assays of the invention. Particularly preferred are cells that grow in a monolayer, as such cells may give more consistent results when used in a fluorescence plate reader. Suitable cells include human embryonic kidney cells (HEK293 cells), COS cells, mouse L cells, Chinese hamster ovary cells, African green monkey kidney cells, Ltk-cells, and BHK cells.

Isolation and Expression of CNG Channel Subunits

Isolation and expression of the olfactory CNG channel subunits or fragments or variants thereof, of the invention can be performed as described below. PCR primers can be used for the amplification of nucleic acids encoding olfactory CNG channel subunits based on the sequence contained in FIG. 1 and libraries of these nucleic acids can thereby be generated. Libraries of expression vectors can then be used to infect or transfect host cells for the functional expression of these libraries. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to mammalian cells, e.g., bacterial, yeast, insect or plant systems.

Alternatively, these nucleic acids can be synthesized in vitro by well-known chemical synthesis techniques, as described in, e.g., Carruthers, *Cold Spring Harbor Symp. Quant. Biol.* 47:411-418 (1982); Adams, *Am. Chem. Soc.* 105:661 (1983); Belousov, *Nucleic Acids Res.* 25:3440-3444 (1997); Frenkel, *Free Radic. Biol. Med.* 19:373-380 (1995); Blommers, *Biochemistry* 33:7886-7896 (1994); Narang, *Meth. Enzymol.* 68:90 (1979); Brown, *Meth. Enzymol.* 68:109 (1979); Beaucage, *Tetra. Lett.* 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., *Molecular Cloning: a Laboratory manual* (2nd ed.), Vols. 1-3, Cold Spring Harbor Laboratory (1989); *Current Protocols in Molecular Biology*, Ausubel, ed. John Wiley & Sons, Inc., New York (1997); Laboratory *Techniques in Biochemistry and Molecular Biology: Hybridization With Nucleic Acid Probes, Part I, Theory and Nucleic Acid Preparation*, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, radioimmunoassay (RIA), enzyme-linked immunosorbent assay (ELISA), immunofluorescent assay, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers are used to amplify nucleic acid encoding an olfactory CNG channel subunit. The nucleic acids described herein can also be cloned or measured quantitatively using amplification techniques. Also using exemplary degenerate primer pair sequences, the skilled artisan can select and design suitable oligonucleotide amplification primers. Amplification methods are also well known in the art, and include, e.g., polymerase chain reaction, PCR (*PCR Protocols, a Guide to Methods and Applications*, ed. Innis. Academic Press, NY, 1990 and *PCR Strategies*, ed. Innis, Academic Press, NY, 1995), ligase chain reaction (LCR) (see, e.g., Wu, *Genomics* 4:560, 1989; Landegren, *Science* 241: 1077, 1988; Barringer, *Gene* 89:117, 1990); transcription amplification (see, e.g., Kwoh, *Proc. Natl. Acad. Sci. USA* 86:1173, 1989); and, self-sustained sequence replication (see, e.g., Guatelli, *Proc. Natl. Acad. Sci. USA* 87:1874, 1990); Q Beta replicase amplification (see, e.g., Smith, *J. Clin. Microbiol.* 35:1477, 1997); automated Q-beta replicase amplification assay (see, e.g., Burg, *Mol. Cell. Probes* 10:257, 1996) and other RNA polymerase mediated techniques (e.g., NASBA, Cangene, Mississauga, Ontario); see also Berger, *Methods Enzymol.* 152:307, 1987; Sambrook; Ausubel; U.S. Pat. Nos. 4,683,195 and 4,683,202; Sooknanan, *Biotechnology* 13:563, 1995.

Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair.

Paradigms to design degenerate primer pairs are well known in the art. For example, a COonsensus-DEgenerate Hybrid Oligonucleotide Primer (CODEHOP) strategy computer program is accessible as http://blocks.fhcrc.org/codehop.html, and is directly linked from the BlockMaker multiple sequence alignment site for hybrid primer prediction beginning with a set of related protein sequences (see, e.g., Rose, *Nucl. Acids Res.* 26:1628, 1998; Singh, *Biotechniques* 24:318, 1998).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, *Nucleic Acids Res.* 25:4866, 1997. Nonpolar molecules can also be used to mimic the shape of natural DNA bases. A non-hydrogen-bonding shape mimic for adenine can replicate efficiently and selectively against a nonpolar shape mimic for thymine (see, e.g., Morales, *Nat. Struct. Biol.* 5:950, 1998). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, *Proc. Natl. Acad. Sci. USA* 95:4258, 1998). Exemplary degenerate primers of the invention incorporate the nucleotide analog 5'-Dimethoxytrityl-N-benzoyl-2'-deoxy-Cytidine, 3'-[(2-cyanoethyl)-(N,N-diisopropyl)]-phosphoramidite (the term "P" in the sequences, see above). This pyrimidine analog hydrogen bonds with purines, including A and G residues.

Nucleic acids that encode olfactory CNG channel subunits are generated by amplification (e.g., PCR) of appropriate nucleic acid sequences using degenerate primer pairs. The amplified nucleic acid can be genomic DNA from any cell or tissue or mRNA or cDNA derived from olfactory receptor-expressing cells, e.g., olfactory neurons or olfactory epithelium.

Isolation of DNAs from olfactory cells is well known in the art, as discussed above, (cells expressing constitutively or inducibly expressing the subject human olfactory CNG channels can be used to screen for compounds that block or modulate smell perception). For example, cells can be identified by olfactory marker protein (OMP), an abundant cytoplasmic protein expressed almost exclusively in mature olfactory sensory neurons (see, e.g., Buiakova, *Proc. Natl. Acad. Sci. USA* 93:9858, 1996). Shirley, *Eur. J. Biochem.* 32:485, 1983), describes a rat olfactory preparation suitable for biochemical studies in vitro on olfactory mechanisms. Cultures of adult rat olfactory receptor neurons are described by Vargas, *Chem. Senses* 24:211, 1999). Also, U.S. Pat. No. 5,869,266 describes culturing human olfactory neurons for neurotoxicity tests and screening. Murrell, *J. Neurosci.* 19:8260, 1999), describes differentiated olfactory receptor-expressing cells in culture that respond to odorants, as measured by an influx of calcium.

Hybrid protein-coding sequences comprising the subject human CNG channel subunits can also be fused to the translocation sequences. Also, these nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, transgenics, and a promoter fragment can be employed to direct expression of the desired nucleic acid in all tissues. Olfactory cell-specific transcriptional elements can also be used to express the fusion polypeptide receptor, including, e.g., a 6.7 kb region upstream of the M4 olfactory receptor coding region. This region was sufficient to direct expression in olfactory epithelium with wild type zonal restriction and distributed neuronal expression for endogenous olfactory receptors (Qasba, *J. Neurosci.* 18:227, 1998). Receptor genes are normally expressed in a small subset of neurons throughout a zonally restricted region of the sensory epithelium. The transcriptional or translational control elements can be isolated from natural sources, obtained from such sources as ATCC or GenBank libraries, or prepared by synthetic or recombinant methods.

Fusion proteins, either having C-terminal or, more preferably, N-terminal translocation sequences, may also comprise the translocation motif described herein. However, these fusion proteins can also comprise additional elements for, e.g., protein detection, purification, or other applications. Detection and purification facilitating domains include, e.g., metal chelating peptides such as polyhistidine tracts or histidine-tryptophan modules or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, *Biochimie* 80:289, 1998), subtilisin protease recognition motif (see, e.g., Polyak, *Protein Eng.* 10:615, 1997); enterokinase (Invitrogen, San Diego, Calif.), and the like, between the translocation domain (for efficient plasma membrane expression) and the rest of the newly translated polypeptide may be useful to facilitate purification. For example, one construct can include a nucleic acid sequence encoding a polypeptide linked to six histidine residues followed by a thioredoxin, an enterokinase cleavage site (see, e.g., Williams, *Biochemistry* 34:1787, 1995), and an amino terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature, see, e.g., Kroll, *DNA Cell. Biol.* 12:441, 1993).

Expression vectors, either as individual expression vectors or as libraries of expression vectors, comprising the olfactory binding domain-encoding sequences may be introduced into a genome or into the cytoplasm or a nucleus of a cell and expressed by a variety of conventional techniques, well described in the scientific and patent literature. See, e.g., Roberts, *Nature* 328:731, 1987; Berger supra; Schneider, *Protein Expr. Purif.* 6435:10, 1995; Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron or Basta) to permit selection of those cells transformed with the desired DNA sequences (see, e.g., Blondelet-Rouault, *Gene* 190:315, 1997; Aubrecht, *J. Pharmacol. Exp. Ther.* 281:992, 1997). Because selectable marker genes conferring resistance to substrates like neomycin or hygromycin can only be utilized in tissue culture, chemoresistance genes are also used as selectable markers in vitro and in vivo.

The present invention also includes not only the DNA and proteins having the specified amino acid sequences, but also DNA fragments, particularly fragments of, for example, 40, 60, 80, 100, 150, 200, or 250 nucleotides, or more, as well as protein fragments of, for example, 10, 20, 30, 50, 70, 100, or 150 amino acids, or more.

Also contemplated are chimeric proteins, comprising at least 10, 20, 30, 50, 70, 100, or 150 amino acids, or more, of at least one of the sensory receptor human CNG channel subunits described herein, and optionally other peptides, e.g., another receptor subunit or a reporter polypeptide. Chimeric receptors are well known in the art, and the techniques for creating them and the selection and boundaries of domains or fragments of different receptors are also well known. Thus, this knowledge of those skilled in the art can readily be used to create such chimeric receptors. The use of such chimeric receptors can provide, for example, an olfactory selectivity characteristic of one of the receptors specifically disclosed herein, coupled with the signal transduction characteristics of another receptor, such as a well known receptor used in prior art assay systems.

Polymorphic variants, alleles, and interspecies homologs that are substantially identical to a human olfactory CNG subunit disclosed herein can be isolated using nucleic acid probes constructed based on the sequences contained in FIG. 1. Alternatively, expression libraries can be used to isolate sensory receptors and polymorphic variants, alleles, and interspecies homologs thereof, by detecting expressed homologs immunologically with antisera or purified antibodies made against a sensory receptor-derived polypeptide, which also recognize and selectively bind to the sensory receptor homolog.

Also within the scope of the invention are host cells for expressing the human CNG channel subunit fragments, or variants of the invention. To obtain high levels of expression of a cloned gene or nucleic acid, such as cDNAs encoding the CNG subunit fragments, or variants thereof, the nucleic acid sequence of interest is subcloned into an expression vector that contains a strong promoter to direct transcription, a transcription/translation terminator, and if for a nucleic acid encoding a protein, a ribosome binding site for translational initiation. Suitable prokaryotic and eukaryotic expression systems are well known in the art and described, e.g., in Sambrook et al.

Any of the well-known procedures for introducing foreign nucleotide sequences into host cells may be used. These include the use of calcium phosphate transfection, polybrene, protoplast fusion, electroporation, liposomes, microinjection, plasmid vectors, viral vectors and any of the other well known methods for introducing cloned genomic DNA, cDNA, synthetic DNA or other foreign genetic material into a host cell (see, e.g., Sambrook et al.). It is only necessary that the particular genetic engineering procedure used be capable of successfully introducing at lest one gene into the host cell capable of expressing the olfactory receptor, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

Immunological Detection of Sensory Receptor Polypeptides

In addition to the detection of human olfactory CNG subunit genes and gene expression using nucleic acid hybridization technology, one can also use immunoassays to detect sensory receptors, e.g., to identify olfactory receptor cells, and variants of sensory receptor family members. Immunoassays can be used to qualitatively or quantitatively analyze the sensory receptors. A general overview of the applicable technology can be found in Harlow & Lane, *Antibodies: A Laboratory Manual* (1988).

Antibodies to Human CNG Olfactory Subunit

Methods of producing polyclonal and monoclonal antibodies that react specifically with a human olfactory CNG subunit family member are known to those of skill in the art (see, e.g., Coligan, *Current Protocols in Immunology*, 1991; Goding, *Monoclonal Antibodies: Principles and Practice*, 2d ed., 1986; Harlow & Lane, supra; and Kohler & Milstein, *Nature*, 256:495, 1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science*, 246:1275, 1989; Ward et al., *Nature*, 341:544, 1989).

A number of immunogens may be used to produce antibody specifically reactive with a particular olfactory CNG subunit family member. For example, a recombinant CNG channel subunit protein, or an antigenic fragment thereof, can be isolated as described herein. Recombinant proteins can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. Mice, hamsters, rats, guinea pigs, rabbits, goats, or chickens can be immunized with the protein using an adjuvant (e.g., Freund's adjuvant) and a standard immunization protocol with periodic boosts. The animal's immune response to the immunogen preparation is monitored by taking test bleeds and determining the titer of reactivity to the sensory receptor. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.*, 6:511, 1976). Alternative methods of immortalization include transformation with Epstein Barr Virus, oncogenes, retroviruses, or other methods well known in the art. Colonies arising from single clones of immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science*, 246:1275, 1989.

Monoclonal antibodies or polyclonal sera are collected and titered against antigen in an immunoassay, for example, a solid phase immunoassay with the antigen immobilized on a solid support. Typically, polyclonal antisera with a titer of $10^4$ or greater are selected and tested for their cross reactivity against non-sensory receptor proteins, or even other sensory receptor family members or other related proteins from other organisms, using a competitive binding immunoassay. Specific polyclonal antisera and monoclonal antibodies will usually bind with a Kd of at least about 0.1 mM, more usually at least about 1 pM, optionally at least about 0.1 pM or better, and optionally 0.01 pM or better.

Once human CNG subunit specific antibodies are available, individual olfactory CNG channel subunit proteins can be detected by a variety of immunoassay methods. For a review of immunological and immunoassay procedures, see *Basic and Clinical Immunology* (Stites & Terr eds., 7th ed., 1991). Moreover, the immunoassays of the present invention can be performed in any of several configurations, which are reviewed extensively in *Enzyme Immunoassay* (Maggio, ed., 1980); and Harlow & Lane, supra.

Immunological Binding Assays

CNG channel subunit proteins can be detected and/or quantified using any of a number of well-recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed., 1991). Immunological binding assays (or immunoassays) typically use an antibody that specifically binds to a protein or antigen of choice (in this case a sensory receptor family member or an antigenic subsequence thereof). The antibody (e.g., anti-sensory receptor) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled sensory receptor polypeptide or a labeled anti-sensory receptor antibody. Alternatively, the labeling agent may be a third moiety, such a secondary antibody, that specifically binds to the antibody/sensory receptor complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.*, 111:1401, 1973; Akerstrom et al., *J. Immunol.*, 135:2589, 1985). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting a protein in a sample may be either competitive or noncompetitive. Noncompetitive immunoassays directly measure the amount of antigen. In one preferred "sandwich" assay, for example, the anti-sensory receptor antibodies are bound directly to a solid substrate on which they are immobilized. These immobilized antibodies then capture the CNG channel subunit protein present in the test sample. The olfactory channel subunit protein thus immobilized is then bound by a labeling agent, such as a second anti-olfactory channel subunit antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of CNG channel subunit protein present in the sample is measured indirectly by measuring the amount of a known, added (exogenous) sensory receptor protein displaced (competed away) from an anti-CNG channel subunit antibody by the unknown olfactory CNG channel subunit protein present in a sample. In one competitive assay, a known amount of CNG channel subunit protein is added to a sample and the sample is then contacted with an antibody that specifically binds to the protein subunit. The amount of exogenous channel subunit protein bound to the antibody is inversely proportional to the concentration of channel subunit protein present in the sample. In a particularly preferred embodiment, the antibody is immobilized on a solid substrate. The amount of protein bound to the antibody may be determined either by measuring the amount of protein present in a subunit/antibody complex, or alternatively by measuring the amount of remaining uncomplexed protein. The amount of protein may be detected by providing a labeled sensory receptor molecule.

A hapten inhibition assay is another preferred competitive assay. In this assay the known channel subunit protein is immobilized on a solid substrate. A known amount of anti-sensory receptor antibody is added to the sample, and the sample is then contacted with the immobilized sensory receptor. The amount of anti-CNG channel subunit antibody bound to the known immobilized CNG subunit protein is inversely proportional to the amount of CNG channel subunit protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for cross-reactivity determinations. For example, a protein at least partially encoded by the nucleic acid sequences disclosed herein can be immobilized to a solid support. Proteins (e.g., CNG subunit proteins and homologs) are added to the assay that compete for binding of the antisera to the immobilized antigen. The ability of the added proteins to compete for binding of the antisera to the immobilized protein is compared to the ability of the CNG channel subunit polypeptide encoded by the nucleic acid sequences disclosed herein to compete with itself. The percentage cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs. In addition, peptides comprising amino acid sequences representing conserved motifs that are used to identify members of the sensory receptor family can be used in cross-reactivity determinations.

The immunoabsorbed and pooled antisera are then used in a competitive binding immunoassay as described above to compare a second protein, thought to be perhaps an allele or polymorphic variant of an olfactory CNG channel subunit family member, to the immunogen protein (i.e., CNG channel subunit protein encoded by the nucleic acid sequences disclosed herein). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by nucleic acid sequences disclosed herein required to inhibit 50% of binding, then the second protein is said to specifically bind to the polyclonal antibodies generated to a sensory receptor immunogen.

Other Assay Formats

Western blot (immunoblot) analysis is used to detect and quantify the presence of olfactory CNG channel subunit protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the sensory receptor protein. The anti-CNG channel subunit polypeptide antibodies specifically bind to the CNG channel subunit polypeptide on the solid support. These antibodies may be directly labeled or alternatively may be subsequently detected using labeled antibodies (e.g., labeled sheep anti-mouse antibodies) that specifically bind to the anti-CNG channel subunit antibodies.

Other assay formats include liposome immunoassays (LIA) using liposomes designed to bind specific molecules (e.g., antibodies) and release encapsulated reagents or markers. The released chemicals are then detected according to standard techniques (see Monroe et al., *Amer. Clin. Prod. Rev.*, 5:34, 1986).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immuno-assays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™, fluorescent dyes (e.g., fluorescein isothiocyanate, Texas red, rhodamine, and the like), radiolabels (e.g., $^3$H, $^{125}$I, $^{35}$S, $^{14}$C, $^{33}$P, or $^{32}$P), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a sensory receptor protein, or secondary antibodies that recognize anti-sensory receptor.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904. Methods for detecting labels are well known. Thus, for example, where the label is a radioactive label, it may be detected using a scintillation counter or with photographic film as in autoradiography. Where the label is a fluorescent label, it may be detected by exciting the fluorochrome with the appropriate wavelength of light and detecting the resulting fluorescence. The fluorescence may be detected visually, with photographic film, or using electronic detectors such as charge coupled devices (CCDs) or photomultipliers. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Fluorescence Polarization Assays

In another embodiment, Fluorescence Polarization ("FP") based assays may be used to detect and monitor binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of odorants to receptors.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labelled oligonucleotide has a relatively low polarization value but when it is hybridized to a complementary strand, it has a higher polarization value. When using FP to detect and monitor odorant-binding which may activate or inhibit the sensory receptors of the invention, fluorescence-labeled sensants or auto-fluorescent sensants may be used.

1. Fluorescence polarization (P) is defined as:

$$P = \frac{Int_\text{||} - Int_\perp}{Int_\text{||} + Int_\perp}$$

Where Π is the intensity of the emission light parallel to the excitation light plane and IntΠ is the intensity of the emission light perpendicular to the excitation light plane. P, being a ratio of light intensities, is a dimensionless number. For example, the Beacon® and Beacon 2000™ System may be used in connection with these assays. Such systems typically express polarization in millipolarization unit (1 Polarization Unit=1100 mP Units).

The relationship between molecular rotation and size is described by the Perrin equation and the reader is referred to Jolley *J. Anal. Toxicol.* 5, 236, 1981 which gives a thorough expla-nation of this equation. Summarily, the Perrin equation states that polarization is directly proportional to the rotational relaxation time, the time that it takes a molecule to rotate through an angle of approximately 68.5°. Rotational relaxation time is related to viscosity (η), absolute temperatrue (T), molecular volume (V), and the gas constant (R) by the following equation:

$$RotationalRelaxationTime = \frac{3\eta V}{RT}$$

The rotational relaxation time is small (≈100 nanosecond) for small molecules (e.g., fluorescein) and large (≈100 nanoseconds) for large molecules (e.g., immunoglobulins). If viscosity and temperature are held constant, rotational relaxation time, and therefore polarization, is directly related to the molecular volume. Changes in molecular volume may be due to inter-actions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

Soluble and Solid State High Throughput Assays

In high throughput assays, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand inter-actions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* 1993). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers (Huntsville, Ala.). The linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149, 1963 (describing solid phase synthesis of, e.g., peptides); Geysen et al., *J. Immun. Meth.* 102:259, 1987 (describing synthesis of solid phase components on pins); Frank & Doring, *Tetrahedron* 44:6031, 1988 (describing synthesis of various peptide sequences on cellulose disks); Fodor et al., *Science* 251:767, 1991; Sheldon et al., *Clinical Chemistry* 39:718, 1993; and Kozal et al., *Nature Medicine,* 2:753, 1996 (all describing arrays of biopolymers fixed to solid substrates). Non-chemical approaches for fixing tag binders to substrates include other common methods, such as heat, cross-linking by UV radiation, and the like.

As noted supra, cell lines will be constructed that express functional CNG channels according to the invention that are activated following odorant stimulation by increases in cAMP or by analogs of cAMP or cGMP. For example, in one embodiment high-throughput CNG plate-based assays will be produced and activated by addition of stimulatory agents to the well. Examples thereof include compounds that stimulate adenylyl cyclase such as forskolin, or by compounds that block phosphodiesterases such as IMBX or by use of membranes permeable analogs of cAMP and cGMP.

In another high-throughput screening protocol, cell-permeable cAMP or cGMP will be delivered via flash photolysis with internal VV illumination to achieve the changes.

Cell-Based Functional Assays

In a preferred embodiment, at least one CNG channel subunit polypeptide polypeptide is expressed in a eukaryotic cell. Such CNG channels can be expressed in any eukaryotic cell, such as HEK-293 cells. Activation of such channels in such cells can be detected, e.g., based on changes in intracellular $Ca^{2+}$.

Samples or assays that are treated with a potential inhibitor or activator are compared to control samples without the test compound, to examine the extent of modulation. Such assays may be carried out in the presence of an odorant that is known to activate the CNG channel by increasing intracellular cAMP or cGMP levels, and modulation of the odorant dependent activation monitored. Control samples (untreated with activators or inhibitors) are assigned a relative sensory receptor activity value of 100. Inhibition is achieved when the sensory receptor activity value relative to the control is about 90%, optionally 50%, optionally 25-0%. Activation is achieved when the channel activity value relative to the control is 110%, optionally 150%, 200-500%, or 1000-2000%.

Changes in ion flux may be assessed by determining changes in polarization (i.e., electrical potential) of the cell or membrane expressing a sensory receptor protein. One means to determine changes in cellular polarization is by measuring changes in current, and thereby measuring changes in polarization, with voltage-clamp and patch-clamp techniques, e.g., the "cell-attached" mode, the "inside-out" mode, and the "whole cell" mode (see, e.g., Ackerman et al., *New Engl. J Med.,* 336:1575, 1997). Whole cell currents are conveniently determined using the standard. Other known assays include: assays to measure ion flux using radiolabeled or fluorescent probes such as voltage-sensitive dyes (see, e.g., Vestergarrd-Bogind et al., *J. Membrane Biol.,* 88:67, 1988; Gonzales & Tsien, *Chem. Biol.,* 4:269, 1997; Daniel et al., *J. Pharmacol. Meth.,* 25:185, 1991; Holevinsky et al., *J. Membrane Biology,* 137:59, 1994) or calcium sensitive dyes such as fluo-3, fluo-4, or fura-2. Generally, the compounds to be tested are present in the range from 1 pM to 100 mM.

In another embodiment, transcription levels can be measured to assess the effects of a test compound on signal transduction. A host cell containing a CNG channel subunit protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the channel subunit protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, '3-galactosidase and alkaline phosphatase. Furthermore, the channel subunit protein of interest can be used as an indirect reporter via attachment to a second reporter such as green fluorescent protein (see, e.g., Mistili & Spector, *Nature Biotech.* 15:961, 1997).

The amount of transcription is then compared to the amount of transcription in either the same cell in the absence of the test compound, or it may be compared with the amount of transcription in a substantially identical cell that lacks the channel subunit protein of interest. A substantially identical cell may be derived from the same cells from which the recombinant cell was prepared but which had not been modified by introduction of heterologous DNA. Any difference in the amount of transcription indicates that the test compound has in some manner altered the activity of the CNG channel.

Transgenic Non-Human Animals Expressing Human Olfactory CNG Channel Subunit

Non-human animals expressing one or more CNG channel subunit sequences of the invention, particularly human olfactory CNG channel sequences, can also be used for assays. Such expression can be used to determine whether a test compound specifically activates a mammalian olfactory CNG channel in vivo by contacting a non-human animal stably or transiently transfected with a nucleic acid encoding an olfactory CNG channel with a test compound and determining whether the animal reacts to the test compound by inhibiting or activating the CNG channel.

Means to infect/express the nucleic acids and vectors, either individually or as libraries, are well known in the art. A variety of individual cell, organ or whole animal parameters can be measured by a variety of means. For example, recording of stimulant-induced waves (bulbar responses) from the main olfactory bulb or accessory olfactory bulb is a useful tool for measuring quantitative stable olfactory responses. When electrodes are located on the olfactory bulb surface it is possible to record stable responses over a period of several days (see, e.g., Kashiwayanagi, *Brain Res. Protoc.* 1:287, 1997). In this study, electroolfactogram recordings were made with a four-electrode assembly from the olfactory epithelium overlying the endoturbinate bones facing the nasal septum. Four electrodes were fixed along the dorsal-to-ventral axis of one turbinate bone or were placed in corresponding positions on four turbinate bones and moved together up toward the top of the bone. See also, Scott, *J. Neurophysiol.* 77:1950, 1997; Scott, *J. Neuro-physiol.* 75:2036, 1996; Ezeh, *J. Neurophysiol.* 73:2207, 1995. In other systems, fluorescence changes in nasal epithelium can be measured using the dye di-4-ANEPPS, which is applied on the rat's nasal septum and medial surface of the turbinates (see, e.g., Youngentob, *J. Neuro-physiol.* 73:387, 1995). Extracellular potassium activity (aK) measurements can also be carried out in in vivo. An increase in aK can be measured in the mucus and the proximal part of the nasal epithelium (see, e.g., Khayari, *Brain Res.* 539:1, 1991).

The olfactory CNG channel sequences of the invention can be for example expressed in animal nasal epithelium by delivery with an infecting agent, e.g., adenovirus expression vector. Recombinant adenovirus-mediated expression of a recombinant gene in olfactory epithelium using green fluorescent protein as a marker is described by, e.g., Touhara, *Proc. Natl. Acad. Sci. USA* 96:4040, 1999. The endogenous CNG channels can remain functional and wild-type (native) activity can still be present. In other situations, where it is desirable that all endogenous CNG channel activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, *Transgenic Res* 6:97, 1997). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem (ES) cells allows one to modify precisely the genomic sequence of interest. Any technique can be used to create, screen for, propagate, a knockout animal, e.g., see Bijvoet, *Hum. Mol. Genet.* 7:53, 1998); Moreadith, *J. Mol. Med.* 75:208, 1997; Tojo, *Cytotechnology* 19:161, 1995; Mudgett, *Methods Mol. Biol.* 48:167, 1995; Longo, *Transgenic Res.* 6:321, 1997; U.S. Pat. Nos. 5,616, 491; 5,464,764; 5,631,153; 5,487,992; 5,627,059; 5,272,071; WO 91/09955; WO93/09222; WO 96/29411; WO 95/31560; WO 91/12650.

The nucleic acid libraries can also be used as reagents to produce "knockout" human cells and their progeny.

Modulators

The compounds tested as modulators of an olfactory CNG channel can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing. of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka, *Int. J. Pept. Prot. Res.* 37:487, 1991; and Houghton et al., *Nature* 354:84, 1991). Other chemistries for generating chemical diversity libraries can also be used. Such chemistries include, but are not limited to: peptoids (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiaze-pines and dipeptides (Hobbs et al., *Proc. Nat. Acad. Sci.* 90:6909, 1993), vinylogous polypeptides (Hagihara et al., *J. Amer. Chem. Soc.* 114:6568, 1992), nonpeptidal peptidomimetics with glucose scaffolding (Hirschmann et al., *J. Amer. Chem. Soc.* 114:9217, 1992), analogous organic syntheses of small compound libraries (Chen et al., *J. Amer. Chem. Soc.* 116:2661, 1994), oligocarbamates (Cho et al., *Science* 261:1303, 1993), peptidyl phosphonates (Campbell et al., *J. Org. Chem.* 59:658, 1994), nucleic acid libraries (Ausubel, Berger and Sambrook, all supra), peptide nucleic acid libraries (U.S. Pat. No. 5,539,083), antibody libraries (Vaughn et al., *Nature Biotechnology* 14:309, 1996 and WO 97/00271), carbohydrate libraries (Liang et al., *Science* 274: 1520, 1996) and U.S. Pat. No. 5,593,853), small organic molecule libraries (benzodiaze-pines, Baum, *C&EN*, page 33, Jan. 18, 1993); thiazolidinones and metathiazanones, U.S. Pat. No. 5,549,974; pynrolidines, U.S. Pat. Nos. 5,525,735 and 5,519,134; morpholino compounds, U.S. Pat. No. 5,506, 337; benzodiazepines, U.S. Pat. No. 5,288,514, and the like.

Devices for the preparation of combinatorial libraries are commercially available (see, e.g., 357 MPS, 390 MPS (Advanced Chem Tech, Louisville, Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

Administration of Novel Smell Modulator (Enhancers or Blockers) Compositions

Sensory modulators can be administered directly to a mammal (e.g., human) for modulation of sensory perception in vivo. Administration is by any of the routes normally used for introducing a modulator compound into ultimate contact with the tissue to be treated (e.g., nose or tongue). The olfactory modulators are administered in any suitable manner, optionally with acceptable carriers. Suitable methods of administering such modulators are available and well known to those of skill in the art, and, although more than one route can be used to administer a particular composition, a particular route can often provide a more immediate and more effective reaction than another route. Acceptable carriers are determined at least in part by the particular components of the composition to be administered (e.g., stabilizing the sensants), as well as by the particular method used to administer the composition. Accordingly, there is a wide variety of suitable formulations of pharmaceutical compositions of the present invention (see, e.g., *Remington's Pharmaceutical Sciences,* 17th ed. 1985).

The sensory modulators, alone or in combination with other suitable components, can be made into aerosol formulations (i.e., they can be "nebulized") to be administered via inhalation. Aerosol formulations can be placed into pressurized acceptable propellants, such as dichloro-difluoromethane, propane, nitrogen, and the like that may or may not contribute to sensory perception. Other possible formulation include dry or liquid forms, powders or tablets, solutions of polar (e.g., water) or nonpolar (e.g., alcohol) solvents, emulsions or suspensions, creams, gels, lotions, and syrups.

Formulations suitable for administration include aqueous and non-aqueous solutions, isotonic sterile solutions, which can contain antioxidants; buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoneally, intravesically, or intrathecally. Optionally, the compositions are administered orally or nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part of a prepared drug, food, or cosmetic. In particular, an unpleasant odor or taste (e.g., sulfur or bitter, respectively) may not be perceived as such and/or its effects reduced by blocking the binding between sensant ligand and sensory receptor by adding a competitor ligand that blocks binding between cognate ligand and receptor, or inhibiting or reducing signal transduction. In contrast, a pleasant odor or taste can be mimicked or enhanced. Primary sensants are preferred because the subset of activated cells is kept small and the effects limited to projection into a specific region of the brain. But novel olfactants or combinations thereof that bind only a few olfactory receptors (e.g., having less than five different ligand-binding domains) would also be useful.

The dose administered to a mammal (e.g., human) should be sufficient to effect a beneficial response in the subject over time. The dose will be determined by the efficacy of the particular sensory modulators employed and the condition of the subject, as well as the body weight or surface area of the area to be treated. The size of the dose also will be determined by the existence, nature, and extent of any adverse side effects that accompany the administration of a particular compound or vector in a particular subject. In determining the effective amount of the modulator to be administered in a physician may evaluate circulating plasma levels of the sensory modulator, modulator toxicities, and the production of anti-modulator antibodies. In general, the dose equivalent of a modulator is from about 1 ng/kg to 10 mg/kg for the typical mammal. For administration, sensory modulators can be administered at a rate determined by the $ED_{50}$ of the modulator, and the side effects of the inhibitor at various concentrations, as applied to the mass and overall health of the mammal. Administration can be accomplished via single or divided doses.

Kits

Human olfactory CNG genes, or fragments or variants thereof are useful tools for identifying cells expressing such channels for forensics and paternity determinations, and for examining signal transduction in isolated cells. Olfactory CNG channel family member-specific reagents that specifically hybridize to oCNG channel nucleic acids, and specific reagents that specifically bind to a CNG channel subunit protein, e.g., anti-CNG channel subunit antibodies are used to examine expression in cells and regulation of signal transduction. For example, one or more family member-specific reagents may be used to detect polymorphisms that are linked to genetic anosmia or to detect allelic exclusion.

Nucleic acid assays for the presence of DNA and RNA for a oCNG channel family member in a sample include numerous techniques are known to those skilled in the art, such as Southern analysis, Northern analysis, dot blots, RNase protection, S1 analysis, amplification techniques such as PCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques,* 4:230-250 (1986); Haase et al., *Methods in Virology,* vol. VII, pp. 189-226 (1984); and *Nucleic Acid Hybridization: A Practical Approach* (Names et al., eds. 1987). In addition, a channel subunit protein can be detected with the various immunoassay techniques described above. The test sample is typically compared to both a positive control (e.g., a sample expressing a recombinant sensory receptor protein) and a negative control.

The present invention also provides for kits for screening for novel modulators of olfactory CNG channels. Such kits can be prepared from readily available materials and reagents, as well as any of the aforementioned products. For example, such kits can comprise any one or more of the following materials: CNG channel encoding nucleic acids or proteins, reaction tubes, and instructions for testing CNG channel activity. A wide variety of kits and components can be prepared according to the present invention, depending upon the intended user of the kit and the particular needs of the user.

The following examples are illustrative of the present invention and should not be interpreted as limiting the applicable scope of the invention in any way.

EXAMPLES

Example 1

Cloning Human Olfactory CNG Channel Subunits

Prior to this invention, the sequences of the human olfactory CNG channel subunits were not known. Electrophysiological analysis of human olfactory neurons, however, suggested a functional similarity to the rat channel (Thurauf et al., 1996), and we identified orthologs of the three rat subunits in the human DNA databank (FIGS. 1-4). We established the presence of OCNC1 and OCNC2 in human olfactory epithelial mRNA by RT-PCR, and the full-length cDNAs for these two subunits were cloned by a combination of PCR from commercially available cDNA and PCR amplification of 5' coding exons from genomic DNA. Terminal 5' AscI and 3' NotI sites were added flanking the human OCNC1 coding sequence, and the OCNC1 AscI-NotI fragment was cloned into the pEAK10 expression vector (Edge Biosystems) to produce plasmid SAV1931. The 5' AscI site incorporated a 3 nucleotide linker sequence to introduce an optimized translation initiation site: GGCGCGCCgccATG (SEQ ID NO: 8), where the AscI site and start ATG are in UPPERCASE and the three-nucleotide linker is in lowercase.

The 3' NotI site was added directly after the stop codon. Human OCNC2 was cloned analogously to produce plasmid SAV1976. Human β1b was cloned similarly to produce plasmid SAV2498; however, the 3 nucleotide linker separating the 5' AscI site and the start ATG was omitted.

Example 2

Developing a High-Throughput Assay Platform for the Human Olfactory CNG Channel

HEK-293T cells were transiently transfected with cloned human olfactory CNG channel subunits using lipid-based protocols. Transfection efficiencies, which were monitored by cotransfection of an RFP expression vector, were typically greater than 70%. After 24 hours, cells were harvested and transferred to 96 well plates. After an additional 24 hours, cells were loaded with either a fluorescent calcium or membrane potential dye for one hour, washed, and transferred to a FLIPR automated fluorometric plate reader with on-board fluidics.

Figure 6:
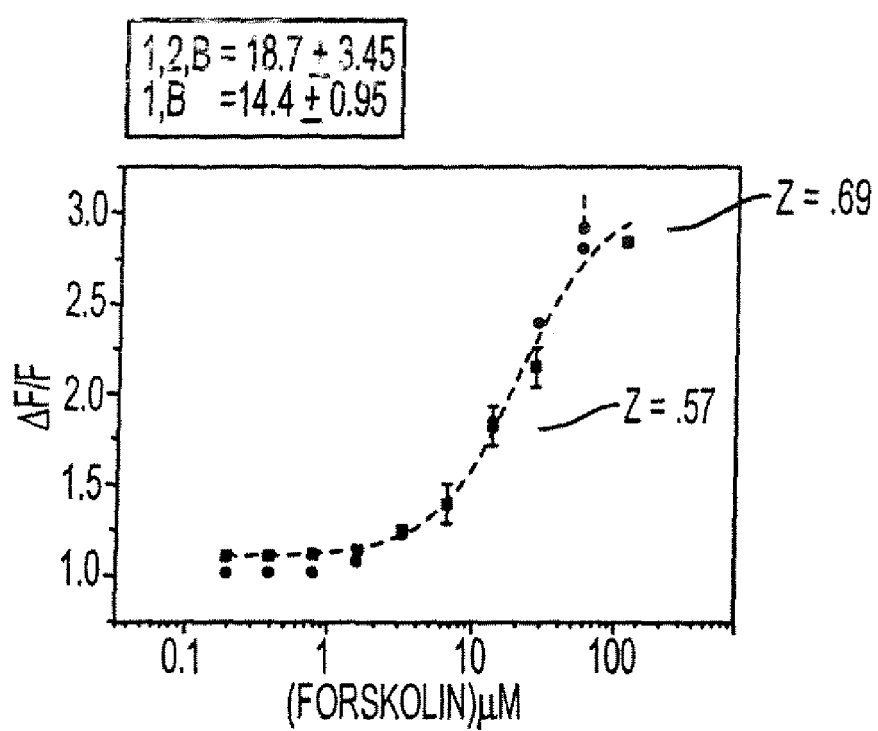
FIG. 6. Membrane-potential-based fluorescent assays for olfactory CNG channel activity are robust. Fluorescence increases at 6 minutes following forskolin addition were determined for cells transfected with different combinations of human olfactory CNG channel subunits and loaded with a membrane-potential dye. Activities represent the mean±s.e. of 8 independent responses and were normalized to fluorescence increases at 6 minutes following addition of KCl. $EC_{50}$ and Z factor values are shown for the two dose-response curves. OCNC1 is abbreviated as '1', OCNC2 as '2', and β1b as 'B'.
Figure 7:
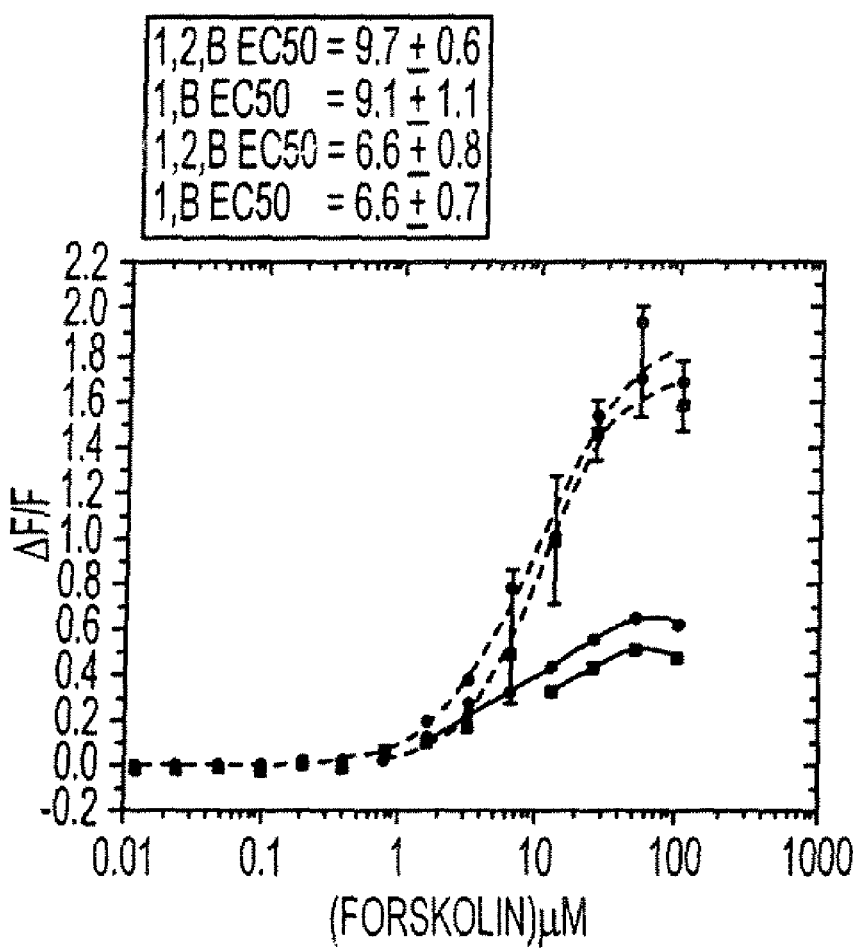
FIG. 7. Calcium-based fluorescent assays for olfactory CNG channel activity are robust. Fluorescence increases at 6 minutes following forskolin addition were determined for cells transfected with different combinations of human olfactory CNG channel subunits and loaded with a membrane-potential dye (black) or a calcium dye (grey). Activities represent the mean±s.e. of 8 independent responses and were normalized to fluorescence increases at 6 minutes following addition of KCl or ionomycin. $EC_{50}$ values are shown for the four dose-response curves. OCNC1 is abbreviated as '1', OCNC2 as '2', and β1b as 'B'.

In contrast to mock-transfected cells, cells transfected with olfactory CNG channel subunits displayed increased fluorescence following forskolin stimulation. Moreover, the magnitude of the forskolin response was subunit dependent: OCNC1 alone produced an active CNG channel, and OCNC2 (to a lesser extent) and β1b (to a greater extent) potentiated OCNC1 activity (FIG. 5). The membrane potential dye provided a better signal to noise ratio than the calcium dye; however, assays using either dye are sufficiently robust for high-throughput screening (FIGS. 6 and 7).

Example 3

Developing a CNG Channel-Based Fluorescence Assay for GPCRs

Figure 8:
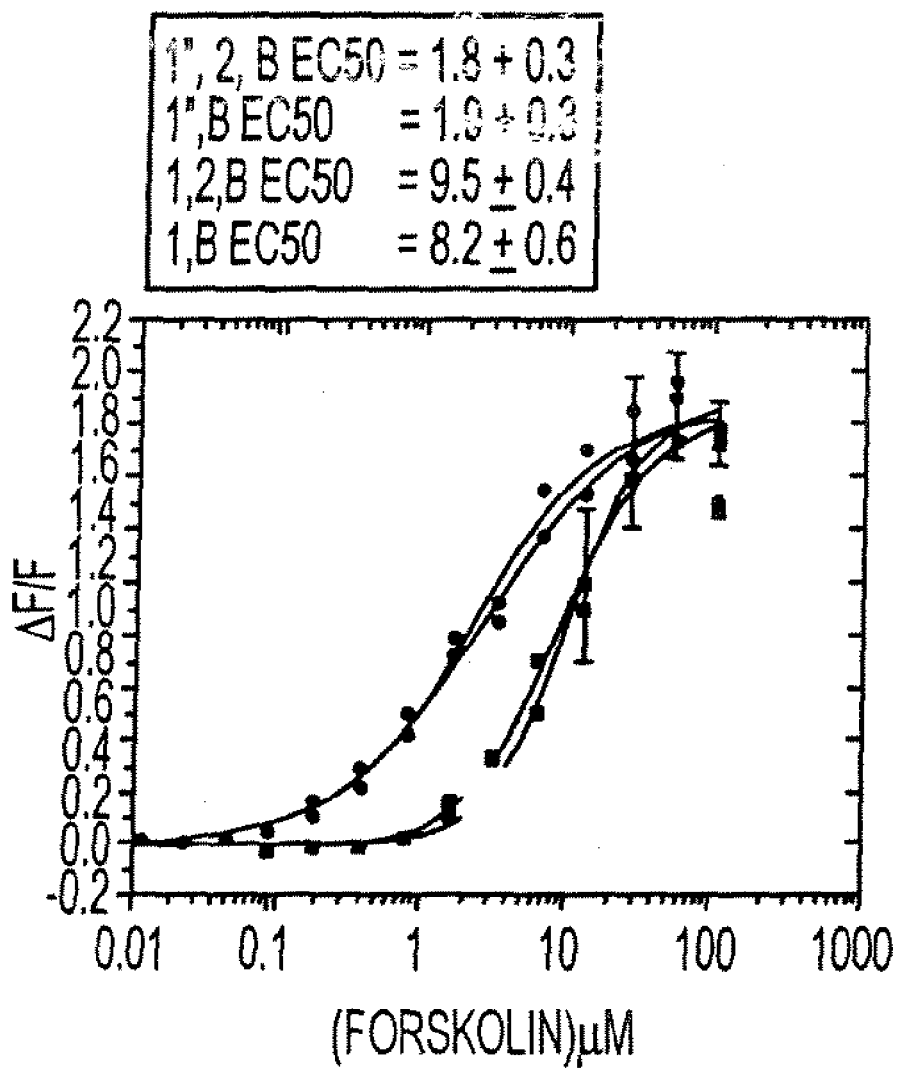
FIG. 8. Human OCNC1[C458W/E581M] and β1b form a sensitized CNG channel. Fluorescence increases at 6 minutes following forskolin addition were determined for cells transfected with different combinations of human olfactory CNG channel subunits and loaded with a membrane-potential dye. Activities represent the mean±s.e. of 8 independent responses and were normalized to fluorescence increases at 6 minutes following addition of KCl. $EC_{50}$ and Z factor values are shown for the two dose-response curves. OCNC1 is abbreviated as '1', OCNC1[C458W/E581M] as '1*', OCNC2 as '2', and β1b as 'B'.

Rich et al. (2001) constructed and characterized a mutant form of the rat OCNC1 CNG channel that has increased cAMP sensitivity. We generated the corresponding hOCNC1 [C460W/E583M] mutant (SEQ ID NO: 4)—carried in plasmid SAV2480—and found that in combination with β1b it has increased cAMP sensitivity and robust activity (FIG. 8). This increased sensitivity suggested that this human olfactory CNG channel variant might function as a cAMP biosensor and allow the development of whole cell-based fluorescence assays for GPCRs and other proteins that regulate cAMP levels.

Figure 9:
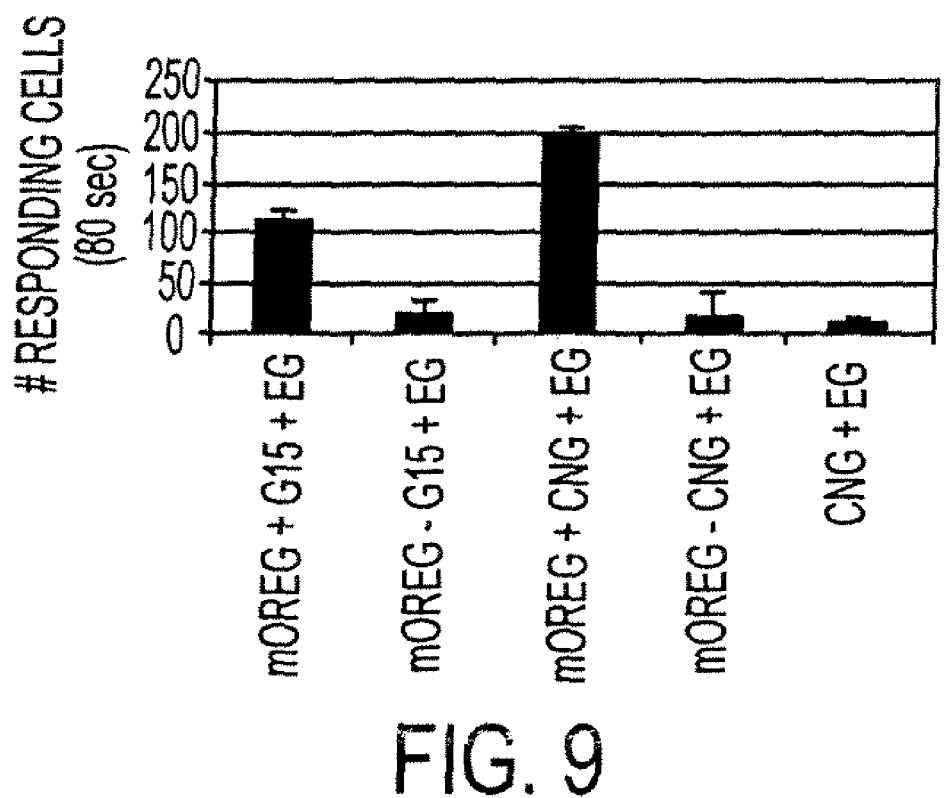
FIG. 9. Olfactory receptor activity can be coupled to the human olfactory CNG channel in heterologous cells. HEK-293 cells were transfected with the mouse olfactory receptor mOREG, OCNC1 [C458W/E581M], OCNC2, and β1b, loaded with a calcium dye, and stimulated with the olfactory stimulus eugenol. The number of responding cells was determined by fluorescence miscroscopy and compared to the number of responding HEK-293 cells transfected with $G_{o15}$ and mOREG; HEK-293 cells transfected with mOREG; and HEK-293 cells transfected with OCNC1[C458W/E581M], OCNC2, and β1.

HEK-293 cells were transfected with OCNC1[C458W/E581FM], OCNC2, and β1b and a mouse olfactory receptor, mOREG, that is activated by eugenol (Kajiya et al., 2001). Transfected cells were seeded onto multi-well plates. After 48 hours, cells were loaded with a calcium dye for one hour, then washed, and their response to eugenol stimulation was monitored by fluorescence microscopy. Eugenol elicited fluorescence increases in transfected cells; this response likely reflects the eugenol-dependent activation of endogenous $G_s$ and adenylyl cyclase by mOREG because comparison to cells transfected with the CNG channel alone or mOREG alone established that these responses were CNG channel dependent and mOREG dependent (FIG. 9).

Example 4

Development of a Cell Line that Stably Expresses the Human Olfactory CNG Channel Subunits OCNC1, OCNC2 and β1b HEK-293 cells were transfected with the three human olfactory CNG channel subunits using lipid-based protocols. The appropriate selection antibiotics were added 72 hours after transfection and single colonies were recovered during a 3-5 week long period after the selection process. Colonies were screened for activity by transient transfection of the mOREG gene and the calcium influx was monitored after stimulation with the mOREG ligand eugenol.

Figure 10:
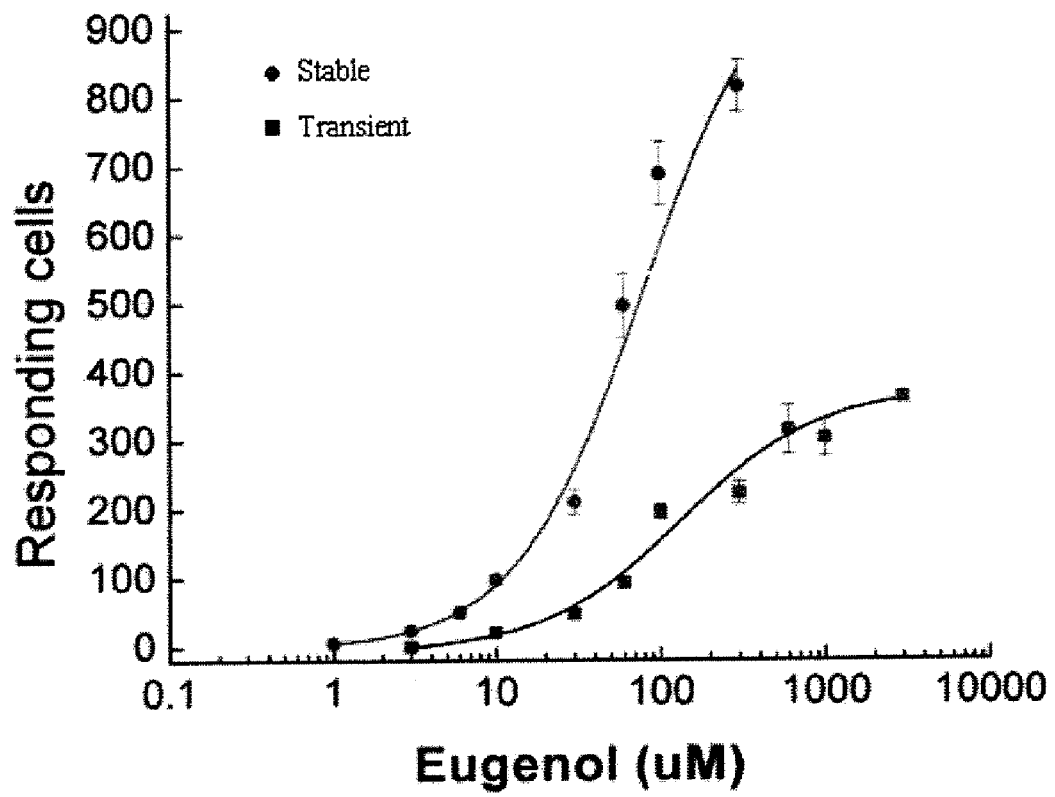
FIG. 10. Stably expressed human CNG channel subunits are more sensitive to eugenol than transiently transfected subunits. HEK-293 cells were stably or transiently expressing the human CNG subunits hOCNC1, hOCNC2 and hβ1b, and transiently transfected with mOREG. The cells were stimulated with various concentrations of eugenol, and calcium influx was measured using Fluo-4 using fluorescent microscopy. Similar result were obtained with the hOCNC1 [C458W/E581M] and β1b subunit (data not shown).

The calcium image assay revealed several clones of cells transfected with the human CNG channel subunits that were responsive to eugenol. In contrast, mock transfected cells had no detectable eugenol response. Expression and activity remain stable after more than 20 passages. Moreover, cells stably expressing the human olfactory CNG subunits are more sensitive to stimulation to eugenol (FIG. 10). Therefore, the cell lines developed are suitable for cell based assays of CNG-mediated calcium transport.

Example 5

Development of a Cell Line that Stably Expresses the Human Olfactory CNG Channel Subunits OCNC1 [C458W/E581M] and β1b HEK-293 cells were transfected with the two human olfactory CNG channel subunits OCNG1 and β1b using lipid-based protocols. The appropriate selection antibiotics were added 72 hours after transfection and single colonies were recovered during a 3-5 week long period after the selection process. Colonies were screened for activity by transiently transfecting the mOREG gene into the cells and monitoring the calcium influx when cells were stimulated whit the mOREG ligand eugenol.

The calcium image assay revealed several clones of cells transfected with the human CNG channel subunits that were responsive to eugenol. In contrast, mock transfected cells had no detectable eugenol response. Expression and activity remain stable after more than 20 passages. In contrast to cells transfected with wild type CNG subunits, the OCNC1 [C458W/E581M] transfected cells displayed significantly higher response to eugenol. Therefore, the cell lines developed are suitable for cell based assays of CNG-mediated calcium transport. Moreover, the increased sensitivity makes the cell line amenable for screens for low affinity agonists or antagonists.

Example 6

Figure 11A:
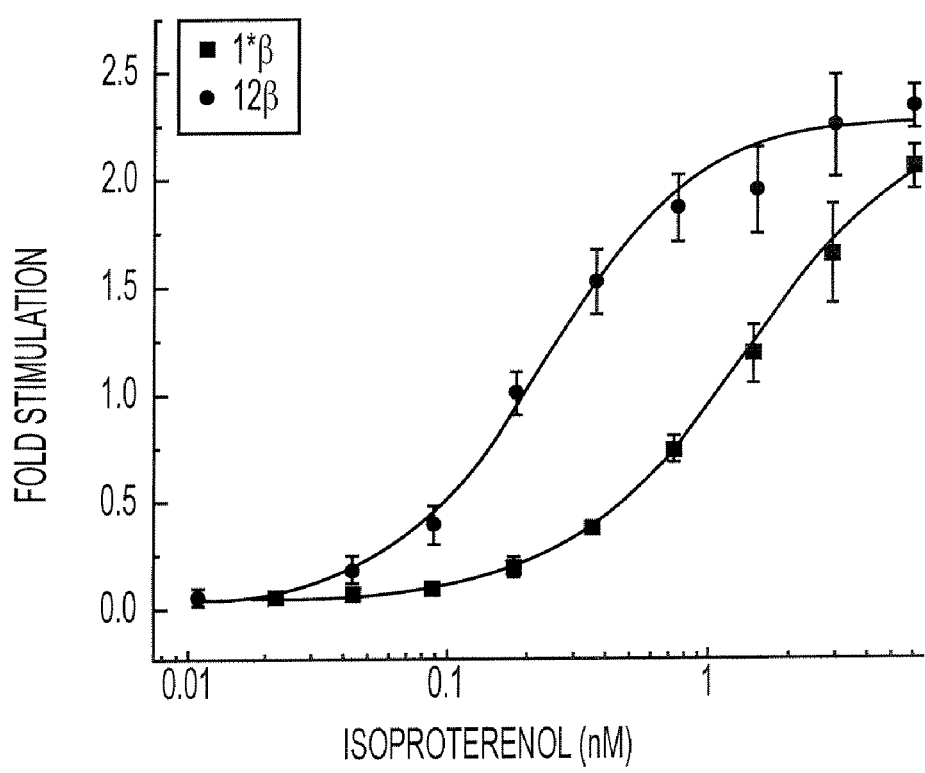
FIG. 11. Stably expressed wild type or enhanced human CNG channel subunits are responsive to receptor mediated activation and adenylyl cyclase activating compounds. In panel (a) of FIG. 11 HEK-293 cells stably expressing either hOCNC1, hOCNC2 and hβ1b, or hOCNC1[C458W/E581M] and β1b, were stimulated with various concentrations of the β2 receptor ligand isoproteranol and the calcium influx was measured using Fluo-4 on a FLIPR-1. In panel (b) of FIG. 11 HEK-293 cells stably expressing either hOCNC1, hOCNC2 and hβ1b, or hOCNC1[C458W/E581M] and β1b, were stimulated with various concentrations of the adenylyl cyclase activator forskolin and the calcium influx was measured using Fluo-4 on a FLIPR-1.
Figure 11B:
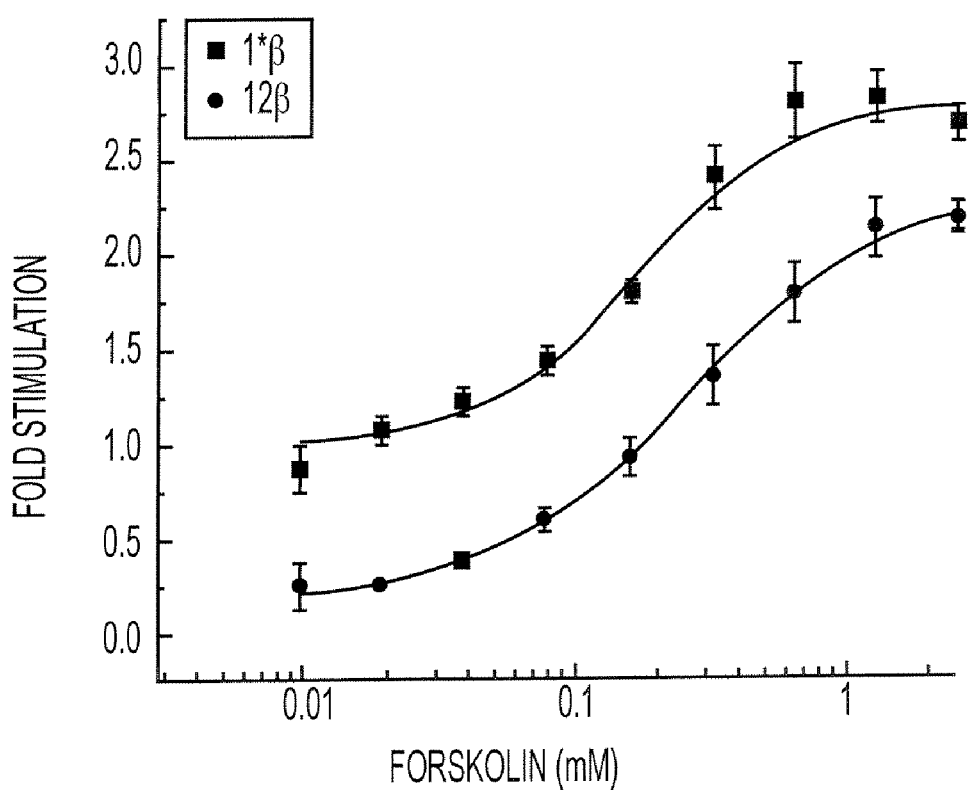

Development of a High-Throughput Assay Platform for the Stably Expressed Human Olfactory CNG Channel Subunits The HEK-293 cells that stably express the human olfactory CNG channel were seeded into FLIPR imaging plates 24 hours prior to the experiment, on plates pre-coated with matrigel. The cells were loaded with a fluorescent calcium dye for one hour, washed and transferred to a FLIPR automated fluorometric plate reader with on-board fluidics. In contrast to the parent cells, cells stably expressing the human olfactory CNG channel subunits displayed increased fluorescence following stimulation of the β2 receptor using isopeteranol (FIG. 11a). Moreover, the cells also showed increased fluorescence following stimulation with the adenylyl cyclase activator forskolin (FIG. 11b). Therefore, the cell-based assay is amenable to high throughput applications.

Example 7

Development of a High-Throughput Assay Platform for an Activity-Enhanced, Stably Expressed Human Olfactory CNG Channel The HEK-293 cells that stably express the activity-enhanced human olfactory CNG channel were seeded into FLIPR imaging plates 24 hours prior to the experiment, on plates pre-coated with matrigel. The cells were loaded with a fluorescent calcium dye for one hour, washed and transferred to a FLIPR automated fluorometric plate reader with on-board fluidics. In contrast to the parent cells and cells transfected with wild type CNG subunits, cells stably expressing the activity-enhanced human olfactory CNG channel subunit displayed increased fluorescence following stimulation with the adenylyl cyclase activator forskolin (FIG. 11b). Moreover, the cells showed fluorescence similar to that observed with wild type CNG subunits following stimulation of the β2 receptor using isopeteranol (FIG. 11a). Therefore, the cell-based assay is amenable to high throughput applications, especially with respect to low affinity agonists and antagonists.

While the invention has been described by way of example embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

REFERENCES

Abe et al. (19920 J. Biol. Chem. 267: 13361-368
Ache B. W. and Zhainazarov, A. (1995) Dual second-messenger pathways in olfactory transduction. Curr. Opin. Neurobiol. 5, 461-466
Adler, E., Hoon, M. A., Mueller, K. L., Chandrashekar, J., Ryba, N. J. P., and Zuker, C. S. (2000) A novel family of mammalian taste receptors. Cell 100, 693-702
Bakalyar, H. A. and Reed R. R. (1990) Identification of a specialized adenylyl cyclase that may mediate odorant detection. Science 250, 1403-1406
Belluscio, L., Gold, G. H., Nemes, A. and Axel, R. Mice deficient in G(olf) are anosmic. Neuron 20, 69-81
Bonigk, W., Bradley, J., Muller, F., Sesti, F., Boekhoff, I., Ronnett, G. V., Kaupp, U. B., and Frings, S. (1999) The native rat olfactory cyclic nucleotide-gated channel is composed of three distinct subunits. J. Neurosci. 19, 5332-5347
Bradley, J., Li, J., Davidson, N., Lester, H. A., and Zinn, K. (1994) Heteromeric olfactory cyclic nucleotide-gated channels: a subunit that confers increased sensitivity to cAMP. Proc. Natl. Acad. Sci. 91, 8890-8894
Breer, H. (1993) Second messenger signalling in olfaction. Ciba Found. Symp. 179, 97-109
Broillet, M.-C. (2000) A single intracellular cysteine residue is responsible for the activation of the olfactory cyclic nucleotide-gated channel by NO, J. Biol. Chem. 275(2): 15135-141
Brown, R. L., Haley, T. L., West, K. A., and Crabb, J. W. (1999) Pseudechetoxin: a peptide blocker of cyclic nucleotide-gated ion channels. Proc. Natl. Acad. Sci. 96, 754-759
Brunet, L. J., Gold, G. H., and Ngai, J. (1996) General anosmia caused by trageted disruption of the mouse olfactory cyclic nucleotide-gated cation channel. Neuron 17, 681-693
Buck, L. and Axel, R. (1991) A novel multigene family may encode odorant receptors: a molecular basis for odor recognition. Cell 65, 175-187
Chen, T. Y., Peng, Y. W., Dhallan, R. S., Ahamed, B., Reed, R. R., and Yau, K. W. (1993) A new subunit of the cyclic nucleotide-gated cation channel in retinal rods. Nature 362, 764-767
Chess, A., Simon, I., Cedar, H., and Axel, R. (1994) Allelic inactivation regulates olfactory receptor gene expression. Cell 78, 823-834
Dhallan, R. S., Yau, K. W., Schrader, K. A., and Reed, R. R. (1990) Primary structure and functional expression of a cyclic nucleotide-activated channel from olfactory neurons. Nature 347, 184-187
Hirono, J., Sato, T., Tonoike, M., Takebayashi, M. (1992) Simultaneous recording of [Ca2+]i increases in isolated olfactory receptor neurons retaining their original spatial relationship in intact tissue. J. Neurosci. Methods 42, 185-194
Hockerman, G. H., Peterson, B. Z., Sharp, E., Tanada, T. N., Scheuer, T., and Catterall, W. A. (1997) Construction of a high-affinity receptor site for dihydropyridine agonists and antagonists by single amino acid substitutions in a non-L-type calcium channel. Proc. Natl. Acad. Sci. 94, 14906-14911
Gold, G. H. (1999) Controversial issues in vertebrate olfactory transduction. Ann. Rev. Physiol. 61, 857-871
Fuchs, T., Glusman, G., Horn-Saban, S., Lancet, D., and Pilpel, Y. (2001) The human olfactory subgenome: from sequence to structure and evolution. Hum. Genet. 108, 1-13
Jones, D. T. and Reed, R. R. (1989) Golf: an olfactory neuron specific-G protein involved in odorant signal transduction. Science 244, 790-795
Kayija, K., Inaki, K. Tanaka, M., Haga, T., Kataoka, H. and Touhara, K. (2001) Molecular bases of odor discrimination: Reconstitution of olfactory receptors that recognize overlapping sets of odorants, J. Neurosci. 21(16): 6018-25.
Kurahashi, T., Lowe, G., and Gold, G. H. (1994) Suppression of odorant responses by odorants in olfactory receptor cells. Science 265, 118-120
Liman, E. R. and Buck, L. B. (1994) A second subunit of the olfactory cyclic nucleotide-gated channel confers high sensitivity to cAMP. Neuron 13, 611-621
Ma, M. and Shepherd, G. M. (2000) Functional mosaic organization of mouse olfactory receptor neurons. Proc. Natl. Acad. Sci. 97, 12869-12874
Malnic, B., Hirono, J., Sato, T., and Buck, L. B. (1999) Combinatorial receptor codes for odors. Cell 96, 713-723

Matsunami, H., Montmayeur, J. P., and Buck, L. B. (2000) A family of candidate taste receptors in human and mouse. Nature 404, 601-604

Meyer, M. R., Angele, A., Kremmer, E., Kaupp, U. B. and Muller, F. (2000) A cGMP-signaling pathway in a subset of olfactory sensory neurons, Proc. Natl. Acad. Sci. USA 97(19): 10595-600.

Murphy, C. (1993) Nutrition and chemosensory perception in the elderly. Crit. Rev. Food Sci. Nutr. 33, 3-15

Nakamura, T. and Gold, G. H. (1987) A cyclic nucleotide-gated conductance in olfactory receptor cilia. Nature 325, 442-444

Nakayasu, C., Kanemura, F., Hirano, Y., Shimizu, Y., and Tonosaki, K. (2000) Sensitivity of the olfactory sense declines with the aging in senescence-accelerated mouse (SAM-P1). Physiol. Behav. 70, 135-139

Qu, W., Zhu, X. O., Moorhouse; A. J., Bieri, S., Cunningham, A. M., and Barry, P. H. (2000) Ion permeation and selectivity of wild-type recombinant rat CNG (rOCNC1) channels expressed in HEK293 cells. J. Membrane Biol. 178, 137-150

Ressler, K. J., Sullivan, S. L., and Buck, L. B. (1994) Information coding in the olfactory system: evidence for a stereotyped and highly organized epitope map in the olfactory bulb. Cell 79, 1245-1255

Rich, T. C., Tse, T. E., Rohan, J. G., Schaak, J., and Karpen, J. W. (2001) In vivo assessment of local phophodiesterase activity using tailored cyclic nucleotide-gated channels as cAMP sensors. J. Gen. Physiol. 118, 63-78

Rolls, B. J. (1993) Appetite, hunger, and satiety in the elderly. Crit. Rev. Food Sci. Nutr. 33, 39-44

Sautter, A., Zong, X., Hofman, F., and Biel, M. (1998) A isoform of the rod photoreceptor cyclic nucleotide-gated channel beta subunit expressed in olfactory neurons. Proc. Natl. Acad. Sci. 95, 4696-4701

Schiffman, S. S. (1993) Perception of taste and smell in elderly persons. Crit. Rev. Food Sci. Nutr. 33, 17-26

Schiffman, S. S. (1997) Taste and smell losses in normal aging and disease. JAMA 278, 1357-1362

Thurauf, N., Gjuric, M., Kobal, G., and Hatt, H. (1996) Cyclic nucleotide-gated channels in identified human olfactory receptor neurons. Eur. J. Neurosci. 8, 2080-2089

Touhara, K., Sengoku, S., Inaki, K., Tsuboi, A., Hirono, J., Sato, T., Sakano, H., and Haga, T. (1999) Functional identification and reconstitution of an odorant receptor in single olfactory neurons. Proc. Natl. Acad. Sci. 96, 4040-4045

Vassar, R., Chao, S. K., Sitcheran, R., Nunez, J. M., Vosshall, L. B., and Axel, R. (1994) Topographic organization of sensory projections to the olfactory bulb. Cell 79, 981-991

Wong, S. T., Trinh, K., Hacker, B., Chan, G. C., Lowe, G., Gaggar, A., Xia, Z., Gold, G. H., and Storm, D. R. (2000) Disruption of the type III adenylyl cyclase gene leads to peripheral and behavioral anosmia in transgenic mice. Neuron 27, 487-497

Zagotta, W. N. and Siegelbaum, S. A. (1996) Structure and function of cyclic nucleotide-gated channels. Ann. Rev. Neurosci. 19, 235-263

Zufall, F. and Leinders-Zufall, T. (2000) The cellular and molecular basis of odor adaptation. Chem. Senses 25, 473-481

What is claimed:

1. An in vitro method for identifying a compound that modulates the activity of a G protein coupled receptor (GPCR) polypeptide by determining the effect of said compound on cyclic nucleotide activated ion mediated transport in a eukaryotic cell expressing said GPCR comprising:
   (i) contacting a recombinant eukaryotic test cell or test cells that expresses (i) a functional cyclic nucleotide gated (CNG) channel, wherein said functional CNG channel comprises an OCNC1 channel subunit polypeptide that is at least 99% identical to the full length OCNC1 polypeptide encoded by the nucleic acid in SEQ ID NO: 1 or 4, said full length OCNC1 polypeptide comprising the OCNC1 polypeptide in SEQ ID NO:9 or 12, an OCNC2 channel subunit polypeptide that is at least 99% identical to the full length OCNC2 polypeptide encoded by the nucleic acid in SEQ ID NO:2, said full length OCNC2 polypeptide comprising the polypeptide in SEQ ID NO:10, and a beta1b olfactory CNG channel subunit polypeptide that is at least 99% identical to the full length beta1b olfactory CNG channel subunit polypeptide encoded by SEQ ID NO:3, said full length beta1b olfactory CNG channel subunit polypeptide comprising the polypeptide and contained in SEQ ID NO:11; and (ii) further expresses a GPCR polypeptide, with a compound that putatively modulates the activity of said GPCR polypeptide;
   (ii) determining the effect of said compound on cyclic nucleotide activated ion transport mediated by said GPCR polypeptide; and
   (iii) identifying the compound as a modulator of said GPCR if it has an effect on cyclic nucleotide activated ion transport mediated by said GPCR polypeptide.

2. The method of claim 1 wherein the GPCR polypeptide is selected from the group consisting of odorant receptors, taste receptors, vomeronasal organ (VNO) receptors, mu opiate receptors, muscarinic acetylcholine receptors, adrenergic receptors, serotonin receptors, dopamine receptors, angiotensin receptors, adenosine receptors, bradykinin receptors, and metabotropic excitatory amino acid receptors.

3. The method of claim 1 wherein the OCNC1 polypeptide comprises a tryptophan at position 458 and/or a methionine at position 581 of the OCNC1 polypeptide encoded by SEQ ID NO:1.

4. The method of claim 3 wherein the OCNC1 polypeptide comprises a tryptophan at position 458 and a methionine at position 581 of the OCNC1 polypeptide encoded by SEQ ID NO:1.

5. The method of claim 1 wherein the eukaryotic test cell is selected from the group consisting of MDCK, HEK, HEK293, HEK293T, BHK, COS, NIH3T3, SWISS3T3 and CHO cells.

6. The method of claim 5 wherein the eukaryotic test cell is an HEK293 or HEK293T cell.

7. The method of claim 1 which comprises a cell-based high throughput assay that uses eukaryotic test cells that express said GPCR and said human CNG channel, wherein the cells are s preloaded with a membrane potential fluorescent dye and at least one putative modulator compound; and monitors changes in fluorescence of the cell in the presence of the putative modulator compound compared to changes in the absence of the putative modulator compound.

8. The method of claim 1 in which said eukaryotic test cells are seeded onto a well of a multi-well test plate.

9. The method of claim 8 wherein said test cells are contacted with a putative modulator by adding said putative modulation to the well of said multi-well test plate.

10. The method of claim 9 wherein said eukaryotic test cells are loaded with a dye that allows for changes in fluorescence to be detected.

11. The method of claim 1 wherein said CNG channels is comprised of subunits that are identical to the full length CNG subunit polypeptides encoded by SEQ ID NO:1 or 4, 2 and 3 respectively, each respectively containing the polypeptides in SEQ ID NO:9 or 12, SEQ ID NO:11 and SEQ ID NO:12.

12. The method of claim 10 wherein a fluorescence plate reader is used to monitor changes in fluorescence.

13. The method of claim 10 wherein a voltage imaging plate reader is used to monitor changes in fluorescence.

14. The method of claim 10 wherein the dye is a membrane potential dye that is selected from the group consisting of Molecular Devices Membrane Potential Kit (cat#R8034), Di-4-ANEPPS (Pyridinium, 4-(2-(6-(dibutylamino)-2-naphthalen-yl)ethenyl)-1-(3-sulfopropyl))-, hydroxide, inner salt), DiSBACC4(2) (bis-(1,2-dibarbituric acid)-trimethine oxanol), DiSBAC4(3) (bis-(1,3-dibarbituric acid)-trimethine oxanol), CC-2-DMPE (Pacific Blue™ 1,2-dietradecanoyl-sn-glycerol-3-phosphoethanolmine, triethylammonium salt) and SBFI-AM (1,3-Benzenedicarboxylic acid, 4,4'-[1,4,10-trioxa-7,13-diazacyclopentadecane-7,13-diylbis(5-methoxy-6, 1-2-benzofurandiyl)]bis-, tettrakis[(acetyloxy)methyl]ester; (Molecular probes).

15. The method of claim 10 wherein said dye is a calcium-sensitive fluorescent dye.

16. The method of claim 1 wherein said GPCR polypeptide is a taste receptor.

17. The method of claim 1 wherein said GPCR is an olfactory receptor.

* * * * *

UNITED STATES PATENT AND TRADEMARK OFFICE
CERTIFICATE OF CORRECTION

| | | |
|---|---|---|
| PATENT NO. | : 8,357,499 B2 | Page 1 of 1 |
| APPLICATION NO. | : 11/326441 | |
| DATED | : January 22, 2013 | |
| INVENTOR(S) | : Zoller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1727 days.

Signed and Sealed this
Twelfth Day of August, 2014

Michelle K. Lee
*Deputy Director of the United States Patent and Trademark Office*